(12) United States Patent
Lal et al.

(10) Patent No.: US 6,692,923 B2
(45) Date of Patent: Feb. 17, 2004

(54) TAPASIN-LIKE PROTEIN

(75) Inventors: Preeti G. Lal, Santa Clara, CA (US); Matthew R. Kaser, Castro Valley, CA (US); Mariah R. Baughn, San Leandro, CA (US)

(73) Assignee: Incyte Corporation, Palo Alto, CA (US)

( * ) Notice: Subject to any disclaimer, the term of this patent is extended or adjusted under 35 U.S.C. 154(b) by 113 days.

(21) Appl. No.: 09/933,561

(22) Filed: Aug. 20, 2001

(65) Prior Publication Data

US 2002/0106664 A1 Aug. 8, 2002

Related U.S. Application Data

(63) Continuation-in-part of application No. 09/292,097, filed on Apr. 14, 1999, now Pat. No. 6,322,977.

(51) Int. Cl.$^7$ .......................... G01N 33/53; A61K 38/00
(52) U.S. Cl. ....................... 435/7.1; 435/7.92; 436/172; 436/501; 436/512; 436/513; 436/547; 436/804; 436/514; 436/2; 436/12; 436/21; 436/530; 436/324; 436/350; 436/827
(58) Field of Search ................................ 514/2, 12, 21; 530/324, 350, 827; 435/7.1, 7.92, DIG. 14; 436/501, 512, 513, 172, 547, 804

(56) References Cited

PUBLICATIONS

Grandea et al. Immunogenetics vol. 48 (Aug. 24, 1998) pp. 260–265.*
Pamer, E., et al., Abstract, Mechanisms of MHC class I—restricted antigen processing, *Annu Rev Immunol,* 16:323–58, (1998).
Ortmann, B., et al., Abstract, A critical role for tapasin in the assembly and function of multimeric MHC class I–TAP complexes, *Science,* 277(5330):1306–9, (1997).
Lewis, JW, et al., Abstract, HLA–A *0201 presents TAP–dependent peptide epitopes to cytotoxic T lymphocytes in the absence of tapasin, *Eur J Immunol,* 28(10):3214–20, (1998).
Suh, WK, et al., Abstract, Interaction of murine MHC class I molecules with tapasin and TAP enhances peptide loading and involves the heavy chain alpha3 domain, *J Immunol,* 162(3):1530–40, (1999).
Lewis, JW, et al., Abstract, Evidence for successive peptide binding and quality control stages during MHC class I assembly, *Curr Biol,* 8 (12) :717–20, (1998).
Grandea, A.G., et al., (Direct Submission), GenBank Sequence Database (Accession AFO43943), National Center for Biotechnology Information, National Library of Medicine, Bethesda, Maryland, 20894 (GI 3169278).
Frangoulis, B., et al., (Direct Submission), GenBank Sequence Database (Accession 3183699), National Center for Biotechnology Information, National Library of Medicine, Bethesda, Maryland, 20894 (GI 3183699).
Elferink, L.A., et al., (Direct Submission), GenBank Sequence Database (Accession M24104 J04827), National Center for Biotechnology Information, National Library of Medicine, Bethesda, Maryland, 20894 (GI 207628).
Ravichandran, V., et al., Identification of a Novel Syntaxin– and Synaptobrevin/VAMP–binding Protein, SNAP–23, Expressed in Non–neuronal Tissues, *The Journal of Biological Chemistry,* 271(23) :13300–13303, (1996).

* cited by examiner

*Primary Examiner*—Bennett Celsa
(74) *Attorney, Agent, or Firm*—Incyte Corporation

(57) ABSTRACT

The invention provides a cDNA which encodes tapasin-like protein. It also provides for the use of the cDNA, protein, and antibody in the diagnosis, prognosis, treatment and evaluation of therapies for cancer. The invention further provides vectors and host cells for the production of the protein and transgenic model systems.

12 Claims, 13 Drawing Sheets

```
                     9              18             27             36             45             54
5' CAC ACA GGG ACG CGG GCT GCC ATC TTG CTC TAA GTG AAA GTG AAA GAA AAG TCG
                    63             72             81             90             99            108
   GCA GCA GAG GGA ACA GGG AAG AAA CCT AAA GGC TGC AGG CTG CCA GGT GTG CTT
                   117            126            135            144            153            162
   GGA GAG CCC CCT TCT TCC GCC GGG CCT CGC AAG CAG CGT AGG ACT GTG GAG AAG
                   171            180            189            198            207            216
   GGC GGT GGG CAA GGA AAC TCG AGA GCA GCC TCC ATG ACA CAG GAG GGC
                                                     M   T   Q   E   G
                   225            234            243            252            261            270
   TGG TGC CTG CTC TGC CTA TCT GGA GCA GAA ACC AAG CCC CAC
    W   C   L   L   C   L   S   G   A   E   T   K   P   H
                   279            288            297            306            315            324
   CCA GCA GAG GGG CAG TGG CGG GCA GTG GAC GTC CTA GAC TGC TTC CTG GCG
    P   A   E   G   Q   W   R   A   V   D   V   L   D   C   F   L   A
                   333            342            351            360            369            378
   AAG GAC GGT GCG CAC CGT GGA GCT CTC GCC AGC AGT GAG GAC AGG GCA AGG GCC
    K   D   G   A   H   R   G   A   L   A   S   S   E   D   R   A   R   A
                   387            396            405            414            423            432
   TCC CTT GTG CTG AAG CAG GTG CCA GTG CTG GAC GAT GGC TCC CTG GAG GAC TTC
    S   L   V   L   K   Q   V   P   V   L   D   D   G   S   L   E   D   F
```

FIGURE 1A

```
       441                 450                 459                 468                 477                 486
ACC GAT TTC CAA       GGG ACA CTG       GCC CAA GAT       GAC CCA CCT       ATT ATC TTT       GAG
 T   D   F   Q         G   T   L         A   Q   D         D   P   P         I   I   F         E 495                 504                 513                 522                 531                 540
GCC TCA GTG GAC       CTG GTC CAG       ATT CCC CAG       GCC GAG TTG       CTC CAT GCT       GAC
 A   S   V   D         L   V   Q         I   P   Q         A   E   L         L   H   A         D 549                 558                 567                 576                 585                 594
TGC AGT GGG AAG       GAG GTG ACC       TGT GAG ATC       TCC CGC TAC       TTT CTC CAG       ATG ACA
 C   S   G   K         E   V   T         C   E   I         S   R   Y         F   L   Q         M   T 603                 612                 621                 630                 639                 648
GAG ACC ACT GTT       AAG ACA GCA       GCT TGG TTC       ATG GCC AAC       ATG CAG GTC       TCT GGA
 E   T   T   V         K   T   A         A   W   F         M   A   N         M   Q   V         S   G 657                 666                 675                 684                 693                 702
GGG GGA CCT AGC       ATC TCC TTG       GTG ATG AAG       ACT CCC AGG       GTC ACC AAG       AAT GAG
 G   G   P   S         I   S   L         V   M   K         T   P   R         V   T   K         N   E 711                 720                 729                 738                 747                 756
GCG CTC TGG CAC       CCG ACG CTG       AAC TTG CCA       CTG AGC CCC       CAG GGG ACT       GTG CGA
 A   L   W   H         P   T   L         N   L   P         L   S   P         Q   G   T         V   R 765                 774                 783                 792                 801                 810
ACT GCA GTG GAG       TTC CAG GTG       ATG ACA CAG       ACC CAA TCC       CTG AGC TTC       CTG CTG
 T   A   V   E         F   Q   V         M   T   Q         T   Q   S         L   S   F         L   L
```

FIGURE 1B

```
        819              828              837              846              855              864
GGG TCC TCA GCC TCC TTG GAC TGT GGC TTC TCC ATG GCA CCG GGC TTG GAC CTC
 G   S   S   A   S   L   D   C   G   F   S   M   A   P   G   L   D   L 873              882              891              900              909              918
ATC AGT GTG GAG TGG CGA CTG CAG CAC AAG GGC AGG GGT CAG TTG GTG TAC AGC
 I   S   V   E   W   R   L   Q   H   K   G   R   G   Q   L   V   Y   S 927              936              945              954              963              972
TGG GCA GCA GGG CAG CAG GCT GTG CGG AAG GGC GCT ACC CTG GAG CCT GCA
 W   T   A   G   Q   Q   A   V   R   K   G   A   T   L   E   P   A 981              990              999              1008             1017             1026
CAA CTG GGC ATG GCC AGG GAT GCC TCC CTC ACC CTG CCC GGC CTC ACT ATA CAG
 Q   L   G   M   A   R   D   A   S   L   T   L   P   G   L   T   I   Q 1035             1044             1053             1062             1071             1080
GAC GAG GGG ACC TAC ATT TGC CAG ATC ACC ACC CTG TAC CGA GCT CAG CAG
 D   E   G   T   Y   I   C   Q   I   T   T   S   L   Y   R   A   Q   Q 1089             1098             1107             1116             1125             1134
ATC ATC CAG CTC AAC ATC CAA GCT TCC CCT AAA GTA CGA CTG AGC TTG GCA AAC
 I   I   Q   L   N   I   Q   A   S   P   K   V   R   L   S   L   A   N 1143             1152             1161             1170             1179             1188
GAA GCT CTG CTG CCC ACC CTC ATC TGC GAC ATT GCT GGC TAT TAC CCT CTG GAT
 E   A   L   L   P   T   L   I   C   D   I   A   G   Y   Y   P   L   D
```

```
      1197              1206              1215              1224              1233         1242
GTG GTG ACG   TGG ACC CGA   GAG GAG CTG   GGT GGA TCC   CCA GCC CAA   GTC TCT
 V   V   T     W   T   R     E   E   L     G   G   S     P   A   Q     V   S 1251              1260              1269              1278              1287         1296
GGT GCC TCC   TTC TCC AGC   CTC AGG CAA   AGC GTG GCA   GGC TAC AGC   ATC TCC
 G   A   S     F   S   S     L   R   Q     S   V   A     G   Y   S     I   S 1305              1314              1323              1332              1341         1350
TCC TCT CTC   ACC GCA GAA   CCT GGC TCT   GCA GGT GCC   ACT TAC ACC   TGC CAG GTC
 S   S   L     T   A   E     P   G   S     A   G   A     T   Y   T     C   Q   V 1359              1368              1377              1386              1395         1404
ACA CAC ATC   TCT CTG GAG   GAG CCC CTT   GGG GCC AGC   ACC CAG GTT   GTC CCA CCA
 T   H   I     S   L   E     E   P   L     G   A   S     T   Q   V     V   P   P 1413              1422              1431              1440              1449         1458
GAG CGG AGA   ACA GCC TTG   GGA GTC ATC   TTT GCC AGC   AGT CTC TTC   CTT CTT GCA
 E   R   R     T   A   L     G   V   I     F   A   S     S   L   F     L   L   A 1467              1476              1485              1494              1503         1512
CTG ATG TTC   CTG CAG CTT   CAG AGA CGG   CAA GCA CCT   ACA GGA CTT   GGG CTG CTT
 L   M   F     L   Q   L     Q   R   R     Q   A   P     T   G   L     G   L   L 1521              1530              1539              1548              1557         1566
CAG GCT GAA   CGC TGG GAG   ACC ACT TCC   TGT GCT GAC   ACA CAG TCC   AGC CAT CTC
 Q   A   E     R   W   E     T   T   S     C   A   D     T   Q   S     S   H   L
```

```
     1575              1584              1593         1602              1611         1620
CAT GAA GAC CGC ACA GCG CGT GTA AGC CAG CCC AGC TGA CCT AAA GCG ACA TGA
 H   E   D   R   T   A   R   V   S   Q   P   S 1629              1638              1647         1656              1665         1674
GAC TAC TAG AAA GAA ACG ACA CCC TTC CCC AAG CCC CCA CAG CTA CTC CAA CCC 1683              1692              1701         1710              1719         1728
AAA CAA CCA AGC CAG TTT AAT GGT AGG AAT TTG TAT TTT TTG CCT TTG TTC 1737              1746              1755         1764
AGA ATA CAT GAC ATT GGT AAA TAT GCC ACA TGC CTT 3'
```

FIGURE 1E

```
103348CB1      ggcagtggcgggcagtggacgtggtcctagactgctgcttcctggcgaaggacggtgcgcaccgtggagctct
2501017F6      ggcagtggcgggcagtggacgtggtcctagactgctgcttcctggcgaaggacggtgcgcaccgtggagctct
                       290            300           310           320           330           340           350

103348CB1      cgccagcagtg*aggacagggcaaggcctccctttgtgctgcagtgcagtgtgctggacgatggctc
2501017F6      cgccagcagtgtaggacagggcaaggcctccctttgtgctgcagtgcagtgtgctggacgatggctc
SASA03761F1    ...........................................................tcccntgaagnaantt
                       360            370           380           390           400           410           420

103348CB1      cctggaggacttcaccgatttccaaggggggcacactgg*cccaagatgacccacct*attatctttgagg
2501017F6      cctggaggacttcaccgatttccaaggggggcacactggncccaagatgacccaactnattaactttgagg
SASA03761F1    caccggatttccaaaggggggncaaaantgcccnaan*gattgaccaacntaat*naacttttgaagc
                       430            440           450           460           470           480           490

103348CB1      cctca*gtggacct*ggtccaga*ttccccaggcc*gaggccttgctcc*atgctgactgcagtgggaag
2501017F6      gctcaagtggacct*ggtccaaaattccccaggcc*gaggctttt..............
SASA03761F1    cntcaagtggaccttggtccccagatccccaagcccgagccctgctcccatgctnactgcagtggaaag
                       500            510           520           530           540           550           560

103348CB1      gaggtgacctgtgagatctcccgctactttctccagatgacagagaccactgttaagacagcagcttgt
SASA03761F1    gagttgacctgtgagatctcccgctacttctctccagatgacagagaccactgttaagacagcagcttggt
                       570            580           590           600           610           620           630

103348CB1      tcatggccaacatgCAGGTCTCTGGAGGGGACCTAGCATCTCCTTGGTGATGAAGACTCCCAGGTCAC
SASA03761F1    tcatggccaacatgCAGGTCTCTGGAGGGGACCTAGCATCTCCTTGGTGATGAAGACTCCCAGGTCAC
SASA01221F1    .....cccaacatgCAGGTCTCTGGAGGGGACCTAGCATCTCCTTGGTGATGAAGACTCCCAGGTCAC
                       640            650           660           670           680           690           700

103348CB1      CAAGAATGAGGcgctctggcacCCGACGCTGAACTTGCCACTGAGCCCCCAGGGACTGTGCGAACTGCA
SASA03761F1    CAAGAATGAGGcgctctggcacCCGACGCTGAACTTGCCACTGAGCCCCCAGGGACTGTGCGAACTGCA
SASA01221F1    CAAGAATGAGGcgctctngcacCCGACGCTGAACTTGCCACTGAGCCCCCAGGGACTGTGCGAACTGCA
                       710            720           730           740           750           760           770
```

FIGURE 2B

```
103348CB1       GTGGAGTTCCAGGTGATGATGACACAGACCCAATCCCTGAGCTTCCTGCTGTGGGTCCTCAGCCTCCTTGACT
SASA03761F1     GTGGAGTTCCAGGTGATGATGACACAGACCCAATCCCTGAGCTTCCTGCTGTGGGTCCTCAGCCTCCTTGACT
SASA01221F1     GTGGAGTTCCAGGTGATGATGACACAGACCCAATCCCTGAGCTTCCTGCTGTGGGTCCTCAGCCTCCTTGACT
SASA01681F1     ..........................................................cggggnttttn
                         780       790       800       810       820       830       840

103348CB1       GTGGCTTCTCCATGGCACCGGGCTTGACCTCATCAGTGTGGAGTGGCAGCTGCAGCACAAGGGCAGGg
SASA03761F1     GTGGCTTCTCCATGGCACCGGGCTTGACCTCATCAGTGTGGAGTGGCAGCTGCAGCACAAGGGCAGGg
SASA01221F1     GTGGCTTCTCCATGGCACCGGGCTTGACCTCATCAGTGTGGAGTGGCAGCTGCAGCACAAGGGCAGGg
SASA01681F1     gaaccctcnaatcaattgttgggaanttngcnaantggccaagcaacaaggngcaaggggttcaagtt
                         850       860       870       880       890       900       910

103348CB1       tcagttggtgtacAGCTGGACCGCAGG**CAGGGGCAGGCTGTGCGAAGGC*GCTACCCctggagcc*
SASA03761F1     tcagttggtgtacAGCTGGACCGCAGG**CAGGGGCAGGCTGTGCGAAGGC*GCTACCctggagngg
SASA01221F1     tcngttggtgtacAGCTGGACCGCAGG**CAGGGGCAGGCTGTGCGAAGGC*GCTACCctggagcc*
SASA01681F1     ngggtgtaacaagcttggaaccgcaggngcagngcagncagnctntgcggaaaggccgctacttggagccc
                         920       930       940       950       960       970       980

103348CB1       tgcACAACTGGGCATGGCCAGggatgcctccctcacCctgcccgcctcacTATACAGGACGAGGGACC
SASA03761F1     nntcctctagagtcgacctgc................................................
SASA01221F1     tgcACAACTGGGCATGGCCAGggatgcctccctcacccctgcccgg........................
SASA01681F1     tgcACAACTGGGCATGGCCAGggatncctccttcaccctgcccgcctcacTATACAGGACGAGGGACC
SASA03117F1     ..............caggtgcgactctagaggntcccccccctcacTATACAGGACGAGGGACC
                         990      1000      1010      1020      1030      1040      1050

103348CB1       TACATTGCCAGATCACCACCTCTCTGTACCGAGCTCAGCAGATCAT*CCAGCTCAACATCCAAGCTTCC
SASA03761F1     TACATTTGCCAGATCACCACCTCTCTGTACCGAGCTCAGCAGATCAT*CCAGCTCAACATCCAAGCTTCC
SASA01221F1     TACATTTGCCAGATCACCACCTCTCTGTACCGAGCTCAGCAGATCAT*CCAGCTCAACATCCAAGCTTCC
SASA01681F1     TACATTTGCCAGATCACCACCTCTCTGTACCGAGCTCAGCAGATCAT*CCAGCTCAACATCCAAGCTTCC
7013222243H1    ........aagctcaacagatcatgcca*cttaacatcctggctccc
                         1060      1070      1080      1090      1100      1110      1120
```

```
103348CB1     CCTAAAGTACGACTGAGCTTGGCAAACGAAGCTCTGCTGCTGCCCACCCTCATTCTGCCACATTGCTGCTATT
SASA01681F1   CCTAAAGTACGACTGAGCTTGGCAAACGAAGCTCTGCTGCTGCCCACCCTCATTCTGCCACATTGCTGCTATT
SASA03117F1   CCTAAAGTACGACTGAGCTTGGCAAACGAAGCTCTGCTGCTGCCCACCCTCATTCTGCCACATTGCTGCTATT
7013222243H1  CCTAAAGTACGACTGAGCTTGGCAAACGAAGCTCTGCTGCTGCCCACCCTCATTCTGCCACATTGCTGCTATT
              cccaaagtacaactgcacttggcaaacaaggatccctcgtcctcccctgcctcctgtctgcagcattgccggctact
                    1130      1140      1150      1160      1170      1180      1190

103348CB1     ACCCTCTGGATGTGGTGGTGGTGGTGACGTGGACGTGGACCCCGAGAGAGAGGAGCTGGGTGATCCCCAGCCCCAAGTCTCTGGTGC
SASA01681F1   ACCCTCTGGATGTGGTGGTGGTGGTGACGTGGACGTGGACCCCGAGAGAGAGGAGCTGGGTGATCCCCAGCCCCAAGTCTCTGGTGC
SASA03117F1   ACCCTCTGGATGTGGTGGTGGTGGTGACGTGGACGTGGACCCCGAGAGAGAGGAGCTGGGTGATCCCCAGCCCCAAGTCTCTGGTGC
7013222243H1  ACCCTCTGGATGTGGTGGTGGTGGTGACGTGGACGTGGACCCCGAGAGAGAGGAGCTGGGTGATCCCCAGCCCCAAGTCTCTGGTGC
2842166T6     atcctctgatgtggagtgacgtgattcgagAGGAGCTGGgtggaattccagcCCAAGTCTCTGGtgc
700294612H1                                                        ...tatgttcctgggcttcagagacg
                    1200      1210      1220      1230      1240      1250      1260

103348CB1     CTCCTTCTCCAGCCTCCAGGCAAAGCGTGGCAGGCACTTACACCTGCCAGGTCACACACACATCTCCTCCTCTCTCTCTCACCGCAgaa*cc
SASA01681F1   CTCCTTCTCCAGCCTCCAGGCAAAGCGTGGCAGGCACTTACACCTGCCAGGTCACACACACATCTCCTCCTCTCTCTCTCACCGCAgaa*cc
SASA03117F1   CTCCTTCTCCAGCCTCCAGGCAAAGCGTGGCAGGCACTTACACCTGCCAGGTCACACACACATCTCCTCCTCTCTCTCTCACCGCAgaa*cc
7013222243H1  CTCCTTCTCCAGCCTCCAGGCAAAGCGTGGCAGGCACTTACACCTGCCAGGTCACACACACATCTCCTCCTCTCTCTCTCACCGCAgaa*cc
              ctc*ttctccagcntcaggcagagcagagcgatggtaacttacagcnttgttcangtgaggctgacca*gc
2842166T6     gcaagagtagaagacaaagagtagttcacgtgctcccagaaagactttaagtcaagtcacagagg*tt
700294612H1   ctccttctccanccctcagaacatgatgggaacctacagcattttcttccacgtgtgannccgannc
                    1270      1280      1290      1300      1310      1320      1330

103348CB1     tggctcTGCAGGTGCCACTTACACCTGCCAGTCACACACACATGCCAGCCCCTTGGGCCAGC
SASA01681F1   tggctcTGCAGGTGCCACTTACACCTGCCAGTCACACACACATGCCAGCCCCTTGGGCCAGC
SASA03117F1   cggctcTGCAGGTGCCACTTACACCTGCCAGTCACACACACATGCCAGCCCCTTGGGCCAGC
7013222243H1  c.........................................
              aaaatacatgaaggtggcaccagtcatgggcactgggcctggcctctgcagaggcctctgcctcctt
2842166T6     
700294612H1   angccncacaggtgcnacttacacctgccaagttgccacgtctccctggccccgtganagtcagc
                    1340      1350      1360      1370      1380      1390      1400
```

```
103348CB1     ACCCAGGTTGTCCCA**C*CAGAGCGGAGAacagccttggggagtcatctttgccagcagtctcttccttc
SASA01681F1   ACCCAGGTTGTCCCA**C*CAGAGCGGAGAacagccttggggagtcctctagat................
SASA03117F1   ACCCAGGTTGTCCCA**C*CAGAGCGGAGAacagccttgggagtcatctttgccagcagtctcttccttc
2842166T6     cactgtgcaccctgg**g*ctcatgcaccaagcagaagaagtgaggggacaagaaggc
7002946l2H1   atganggttttgccaaacacagagagcacanagaggagccttgggagtcatcgttgccancatccctcttncttt
7002513417H1  ...gttttgccaaac**a*cagagcaaagaggagccttgggagtcatcgttgccagcatcctcctcctttt
                          1410        1420        1430        1440        1450        1460        1470

103348CB1     ttgcactgatgttcctggggc**ttcagagacgg*caagca*cctacagg*actt**gggct*gctt*ca
SASA03117F1   ttgcactgatgtncctggggg tttcagagacggggtcaacctataggactttggggcttgctttca
2842166T6     agaatgtccagatggaggata**agaccaaagag*ccagca*cctacagg*actt**gggct*gctt*aa
7002946l2H1   ttgngctctcctgctcctgggac**ttcntngacag*naagct*tcatcatc*anag**ttcnn*caag*tc
7002513417H1  ttgcgctcttgctcctcctgggac**ttcatagacag*caagct*tcancatc*aaag**tccac*caag*tc
                          1480        1490        1500        1510        1520        1530        1540

103348CB1     ggctgaa*cgct*ggga*gacc*acttcctgtgctgacacacagagctccatctccatgaagaccgcac
SASA03117F1   ggctgaaacgcttgggaagaagaccccactnccctgggccnganananaana.............
2842166T6     ggctgaa*cgct*ggga*gacc*gacc*acttcctgtgctgacacacagagctccatctccatgaagaccgcac
7002946l2H1   tgtgagg*nact*ctga*gtag*gtag*ncgctttnctgcc..........................
7002513417H1  tgtgagg*cact*ctga*gtag*gtag*ccgcttcctgcctccgagtacaaagaaaagctctcgtgttctagct
                          1550        1560        1570        1580        1590        1600        1610

103348CB1     agcgcgtgtaagccagcccagctgacctaaagcgacatgagactagaaagaaacgacaccctccccc
2842166T6     agcgcgtgtaagccagcccagctgacctaaagcgacatgagactactagaagaaacgacaccctccccc
7002513417H1  acctaagaaccctgttgaggtgtgggactgagacggcctgaaggaggcagcacattgggagtgaggt
                          1620        1630        1640        1650        1660        1670        1680
```

FIGURE 2E

```
103348CB1       aagccccccacagctactccaaacccaaacaacaaccaagccagtttaatggtaggaatttgtattttttgc.........
2842166T6       aagccccnacagctactccaaacccaaacaacaaccaagccagtttaatggtaggaatttgtattttttgc.........
7002946l2H1     ...........................................................................
7002513477H1    ..actgaccctggtctgtactagtctctgcc.................................................
7002554399H1    ........................................tttgtggtaggaatttgtattttcgc
                    1690      1700      1710      1720      1730      1740      1750

103348CB1       ctttgttcagaatacatgacattggtaaatatgccacatgcctt.............
2842166T6       ctttgttcagaatacatgacattggtaaatatgccacatgcctt.............
7002554399H1    ctttgttgagaatacatgagattggtaaatctgtcacatgccctttggtgaaggacnactcttactacta
                    1760      1770      1780      1790      1800      1810      1820

7002554399H1    tacataaactgtgagactgggttaggaaagacacggtggtaatgacagacacaatggaaaccccacatca
                    1830      1840      1850      1860      1870      1880      1890

7002554399H1    cctcatggcaaacaaagaggatgtgggaagcttggcttcaactga.............
                    1900      1910      1920      1930      1940      1950      1960
```

FIGURE 2F

```
  1  MGTQEGWCLLLCLALSGAAETKPHPAEGQWRAVDVVLDCF            103348
  1  MKPLL---LLVAVALGLATFVSVVSAGPE------AIECW            g3169279
  1  MAAGL---RLL-----------LAGGGAR-----G----            g3183699

41  LAKDGAHRGALASSEDRARASLVLKQVPVLDDGSLEDFTD            103348
 32  FVEDAG----GGGLSKKPATLLLLRHGPRGPPPR-----            g3169279
 17  ---RAA----GGGQCPSCTAALW--GGRGDPSR-----            g3183699

81  FQGGTLAQDDPPIFEASVDLVQIPQAEALLHADCSGKEV            103348
 61  ----PDLDPKLYFKVDDPAGMLLAAFRRYPAGASAPH-            g3169279
 41  --TRPGARSHLQCQRPLGD--SSPTRVPP-RTPPS--            g3183699

121  TCEISRYFLQMTETTVKTAAWFMANMQVSGGGPSIS---            103348
 94  -CEMSRF------IPFPASAKWARSLSPEQNCPRALDGDWL           g3169279
 71  -CELNPT------NPQTGSDPWSRPLHPDARSPPTAGGQWW           g3183699

157  LVMKTPRVTKNEALWHPTLNLPLSPQGTV-RTAVEFQVMT            103348
128  LVSVSSTLFSLSSLLRPQE-PLREPVVITMATVVLTVLT             g3169279
105  VAAVGTPQYGVTALLQ-G-GMGTEGTIT-AAVALAVLT              g3183699

196  QTQSLSFLLGSSASLD--CGFSMA----PGLDL---IS              103348
167  HNPAPRVQLGKDAVLDLRFAYAPSALEGSPSLDAGPPPFG            g3169279
140  HTPTLRARVG--SPIHLHCAFAAAP---PSSFV                   g3183699

225  VEWRLQHKGRGQLVYSWTAGQGQAVRKGATLEPAQLGMAR            103348
207  LEWRRQHRGKGHLL--AATPGLAGRMPPAQEKATAFAAW             g3169279
167  LEWRHQNRGAGRVLL--AYDSS-TARAPRAHPGAELLGT             g3183699
```

FIGURE 3A

```
265  D--------ASLTLPGLTIQDEGTYICQITTSLYRAQ                                    103348
245  DDDEPWGPWTGNGTFWLPAVKPSQEGVYLGTVHLPYLQGQ                                 g3169279
204  RDGDG---VTAVTLRLARPSPGDEGTYICSVFLPHGHTQ                                  g3183699

294  QIQLNIQASPKVRLS-----LANEALLPTLICDIAGYY                                   103348
285  VSLELTVHKGPRVSLTPAPVVWAAPGEAPPELLCLASHFF                                 g3169279
240  TVLQLHVFEPPKVTLSPKNLV-VAPG-TSAELRCHVSGFY                                 g3183699

328  PLDVV-VTWTREELGGSPAQ---VSGASFSSLRQSVAG                                   103348
325  PAEGLEVKWELRGGPGGSS---RKVEGKTWLSTIRHHSDG                                  g3169279
278  PLD-VTVTWQRRAGGSGTSQSPRDTVMDSWTSGHRQAADG                                  g3183699

362  TYSISSSLTAEPGSA--GATYTCQVTHISLEEPLGASTQ                                   103348
362  SVSQSGHLQLPPVTAKQHGVHYVCRVYHSSLPASGRSADV                                  g3169279
317  TYSRTAAARLIPARPQHHGDIYSCVVTHTALAKPMR-VSV                                  g3183699

399  VVPPERRTALGVIFASSLFLLALMFLGLQRRQAPTGLGLL                                  103348
402  TLEVAGFSGPSIEDGIGLFLSAFLLLGLLK----VLGWL                                   g3169279
356  RLLAGTEGPHLEDITGLFLVAFVLCGLIR----------                                   g3183699

439  QAERWETTSCADTQSSHLHEDRTARVSQPS                                            103348
437  AAY-WTIPEVSKEKATAASLTIPRNSKKSQ                                           g3169279
386  ----WLYPKAARPKE------ETKKSQ                                              g3183699
```

FIGURE 3B

SEQUENCE LISTING

```
<160> NUMBER OF SEQ ID NOS: 17

<210> SEQ ID NO 1
<211> LENGTH: 1764
<212> TYPE: DNA
<213> ORGANISM: Homo sapiens
<220> FEATURE: -
<223> OTHER INFORMATION: 103348CB1

<400> SEQUENCE: 1
cacacaggga cgcgggctgc catcttgctc taagtgaaag tgaaagaaaa gtcggcagca      60
gagggaacag ggaagaaacc taaaggctgc aggctgccag gtgtgcttgg agagccccct     120
tcttccgccg ggcctcgcaa gcagcgtagg actgtggaga agggcggtgg gcaaggaggg     180
aactcgagag cagcctccat gggcacacag gagggctggt gcctgctgct ctgcctggct     240
ctatctggag cagcagaaac caagcccac ccagcagagg ggcagtggcg ggcagtggac      300
gtggtcctag actgcttcct ggcgaaggac ggtgcgcacc gtggagctct cgccagcagt     360
```

-continued

```
gaggacaggg caagggcctc ccttgtgctg aagcaggtgc cagtgctgga cgatggctcc    420
ctggaggact tcaccgattt ccaaggggc acactggccc aagatgaccc acctattatc    480
tttgaggcct cagtggacct ggtccagatt ccccaggccg aggccttgct ccatgctgac    540
tgcagtggga aggaggtgac ctgtgagatc tcccgctact ttctccagat gacagagacc    600
actgttaaga cagcagcttg gttcatggcc aacatgcagg tctctggagg gggacctagc    660
atctccttgg tgatgaagac tcccagggtc accaagaatg aggcgctctg cacccgacg    720
ctgaacttgc cactgagccc ccaggggact gtgcgaactg cagtggagtt ccaggtgatg    780
acacagaccc aatccctgag cttcctgctg gggtcctcag cctccttgga ctgtggcttc    840
tccatggcac cgggcttgga cctcatcagt gtggagtggc gactgcagca aagggcagg     900
ggtcagttgg tgtacagctg gaccgcaggg caggggcagg ctgtgcggaa gggcgctacc    960
ctggagcctg cacaactggg catggccagg gatgcctccc tcaccctgcc cggcctcact   1020
atacaggacg aggggaccta catttgccag atcaccacct ctctgtaccg agctcagcag   1080
atcatccagc tcaacatcca agcttcccct aaagtacgac tgagcttggc aaacgaagct   1140
ctgctgccca ccctcatctg cgacattgct ggctattacc ctctggatgt ggtggtgacg   1200
tggacccgag aggagctggg tggatcccca gcccaagtct ctggtgcctc cttctccagc   1260
ctcaggcaaa gcgtggcagg cacctacagc atctcctcct ctctcaccgc agaacctggc   1320
tctgcaggtg ccacttacac ctgccaggtc acacacatct ctctggagga gccccttggg   1380
gccagcaccc aggttgtccc accagagcgg agaacagcct gggagtcat ctttgccagc    1440
agtctcttcc ttcttgcact gatgttcctg gggcttcaga gacggcaagc acctacagga   1500
cttgggctgc ttcaggctga acgctgggag accacttcct gtgctgacac acagagctcc   1560
catctccatg aagaccgcac agcgcgtgta agccagccca gctgacctaa agcgacatga   1620
gactactaga aagaaacgac accttcccc aagccccac agctactcca acccaaacaa    1680
caaccaagcc agtttaatgg taggaatttg tattttttgc ctttgttcag aatacatgac   1740
attggtaaat atgccacatg cctt                                          1764
```

<210> SEQ ID NO 2
<211> LENGTH: 468
<212> TYPE: PRT
<213> ORGANISM: Homo sapiens
<220> FEATURE: -
<223> OTHER INFORMATION: 103348CD1

<400> SEQUENCE: 2

```
Met Gly Thr Gln Glu Gly Trp Cys Leu Leu Cys Leu Ala Leu
  1               5                  10                  15

Ser Gly Ala Ala Glu Thr Lys Pro His Pro Ala Glu Gly Gln Trp
                 20                  25                  30

Arg Ala Val Asp Val Leu Asp Cys Phe Leu Ala Lys Asp Gly
                 35                  40                  45

Ala His Arg Gly Ala Leu Ala Ser Ser Glu Asp Arg Ala Arg Ala
                 50                  55                  60

Ser Leu Val Leu Lys Gln Val Pro Val Leu Asp Asp Gly Ser Leu
                 65                  70                  75

Glu Asp Phe Thr Asp Phe Gln Gly Gly Thr Leu Ala Gln Asp
                 80                  85                  90

Pro Pro Ile Ile Phe Glu Ala Ser Val Asp Leu Val Gln Ile Pro
                 95                 100                 105
```

```
Gln Ala Glu Ala Leu Leu His Ala Asp Cys Ser Gly Lys Glu Val
            110                 115                 120

Thr Cys Glu Ile Ser Arg Tyr Phe Leu Gln Met Thr Glu Thr Thr
            125                 130                 135

Val Lys Thr Ala Ala Trp Phe Met Ala Asn Met Gln Val Ser Gly
            140                 145                 150

Gly Gly Pro Ser Ile Ser Leu Val Met Lys Thr Pro Arg Val Thr
            155                 160                 165

Lys Asn Glu Ala Leu Trp His Pro Thr Leu Asn Leu Pro Leu Ser
            170                 175                 180

Pro Gln Gly Thr Val Arg Thr Ala Val Glu Phe Gln Val Met Thr
            185                 190                 195

Gln Thr Gln Ser Leu Ser Phe Leu Leu Gly Ser Ser Ala Ser Leu
            200                 205                 210

Asp Cys Gly Phe Ser Met Ala Pro Gly Leu Asp Leu Ile Ser Val
            215                 220                 225

Glu Trp Arg Leu Gln His Lys Gly Arg Gly Gln Leu Val Tyr Ser
            230                 235                 240

Trp Thr Ala Gly Gln Gly Gln Ala Val Arg Lys Gly Ala Thr Leu
            245                 250                 255

Glu Pro Ala Gln Leu Gly Met Ala Arg Asp Ala Ser Leu Thr Leu
            260                 265                 270

Pro Gly Leu Thr Ile Gln Asp Glu Gly Thr Tyr Ile Cys Gln Ile
            275                 280                 285

Thr Thr Ser Leu Tyr Arg Ala Gln Gln Ile Ile Gln Leu Asn Ile
            290                 295                 300

Gln Ala Ser Pro Lys Val Arg Leu Ser Leu Ala Asn Glu Ala Leu
            305                 310                 315

Leu Pro Thr Leu Ile Cys Asp Ile Ala Gly Tyr Tyr Pro Leu Asp
            320                 325                 330

Val Val Val Thr Trp Thr Arg Glu Glu Leu Gly Gly Ser Pro Ala
            335                 340                 345

Gln Val Ser Gly Ala Ser Phe Ser Ser Leu Arg Gln Ser Val Ala
            350                 355                 360

Gly Thr Tyr Ser Ile Ser Ser Ser Leu Thr Ala Glu Pro Gly Ser
            365                 370                 375

Ala Gly Ala Thr Tyr Thr Cys Gln Val Thr His Ile Ser Leu Glu
            380                 385                 390

Glu Pro Leu Gly Ala Ser Thr Gln Val Val Pro Pro Glu Arg Arg
            395                 400                 405

Thr Ala Leu Gly Val Ile Phe Ala Ser Ser Leu Phe Leu Leu Ala
            410                 415                 420

Leu Met Phe Leu Gly Leu Gln Arg Arg Gln Ala Pro Thr Gly Leu
            425                 430                 435

Gly Leu Leu Gln Ala Glu Arg Trp Glu Thr Thr Ser Cys Ala Asp
            440                 445                 450

Thr Gln Ser Ser His Leu His Glu Asp Arg Thr Ala Arg Val Ser
            455                 460                 465

Gln Pro Ser

<210> SEQ ID NO 3
<211> LENGTH: 258
<212> TYPE: DNA
<213> ORGANISM: Homo sapiens
```

```
<220> FEATURE: -
<223> OTHER INFORMATION: 103348H1
<221> NAME/KEY: unsure
<222> LOCATION: 9, 61, 68, 123, 131, 196, 214, 218, 246, 248
<223> OTHER INFORMATION: a, t, c, g, or other

<400> SEQUENCE: 3
ctacatttnc cagatcacca cctctctgta ccgagctcag cagatcatcc agctcaacat      60
ncaagctncc cctaaagtac gactgagctt ggcaaacgaa gctctgctgc ccaccctcat     120
ctncgacatt nctggctatt accctctgga tgtggtggtg acgtggaccc gagaggagct    180
gggtggattc cccagnccaa gtttctggtg cctncttntc cagcctcagg caaagcgttg    240
gcaggnanct acagcata                                                  258

<210> SEQ ID NO 4
<211> LENGTH: 533
<212> TYPE: DNA
<213> ORGANISM: Homo sapiens
<220> FEATURE: -
<223> OTHER INFORMATION: 2501017F6
<221> NAME/KEY: unsure
<222> LOCATION: 401, 459, 477
<223> OTHER INFORMATION: a, t, c, g, or other

<400> SEQUENCE: 4
cacacaggga cgcgggctgc catcttgctc taagtgaaag tgaaagaaaa gtcggcagca     60
gagggaacag ggaagaaacc taaaggctgc aggctgccag gtgtgcttgg agagccccct   120
tcttccgccg ggcctcgcaa gcagcgtagg actgtggaga agggcggtgg caaggaggg    180 aactcgagag cagcctccat gggcacacag gagggctggt gcctgctgct ctgcctggct   240
ctatctggag cagcagaaac caagccccac ccagcagagg ggcagtggcg ggcagtggac   300
gtggtcctag actgcttcct ggcgaaggac ggtgcgcacc gtggagctct cgccagcagt   360
gtaggacagg gcaagggcct cccttgtgct gaagcaggtg ncagtgctgg acgatggctc   420
cctggaggac ttcaccgatt tccaaggggg cacactggnc caagatgac ccaactnatt    480 aactttgagg gctcaagtgg acctggtcca aaattcccca ggccgaggct ttt          533

<210> SEQ ID NO 5
<211> LENGTH: 593
<212> TYPE: DNA
<213> ORGANISM: Homo sapiens
<220> FEATURE: -
<223> OTHER INFORMATION: SASA03761F1
<221> NAME/KEY: unsure
<222> LOCATION: 20, 21, 24, 453, 479, 507, 521, 526, 539, 542, 549, 555,
      579, 582, 589
<223> OTHER INFORMATION: a, t, c, g, or other

<400> SEQUENCE: 5
gcaggtcgac tctagaggan nccnctccag ggtagcgccc ttccgcacag cctgcccctg     60
ccctgcggtc cagctgtaca ccaactgacc cctgcccttg tgctgcagtc gccactccac   120
actgatgagg tccaagcccg gtgccatgga gaagccacag tccaaggagg ctgaggaccc   180
cagcaggaag ctcagggatt gggtctgtgt catcacctgg aactccactg cagttcgcac   240
agtcccctgg gggctcagtg gcaagttcag cgtcgggtgc cagagcgcct cattcttggt   300
gaccctggga gtcttcatca ccaaggagat gctaggtccc cctccagaga cctgcatgtt   360
ggccatgaac caagctgctg tcttaacagt ggtctctgtc atctggagaa agtagcggga   420
gatctcacag gtcaactcct ttccactgca gtnagcatgg gagcaagggc tcgggcttng   480
```

```
gggatcttgg accaaggtcc acttganggc ttcaaaagtt nattangttg ggtcaatcnt    540
tngggccant tttgnccccc tttggaaaat ccggtgaant tncttccang gga           593
```

<210> SEQ ID NO 6
<211> LENGTH: 386
<212> TYPE: DNA
<213> ORGANISM: Homo sapiens
<220> FEATURE: -
<223> OTHER INFORMATION: SASA01221F1
<221> NAME/KEY: unsure
<222> LOCATION: 109, 304
<223> OTHER INFORMATION: a, t, c, g, or other

<400> SEQUENCE: 6

```
ccgggcaggg tgagggaggc atccctggcc atgcccagtt gtgcaggctc cagggtagcg    60
cccttccgca cagcctgccc ctgccctgcg gtccagctgt acaccaacng acccctgccc   120
ttgtgctgca gtcgccactc cacactgatg aggtccaagc ccgtgccat ggagaagcca    180 cagtccaagg aggctgagga ccccagcagg aagctcaggg attgggtctg tgtcatcacc   240
tggaactcca ctgcagttcg cacagtcccc tggggctca gtggcaagtt cagcgtcggg    300
tgcnagagcg cctcattctt ggtgaccctg ggagtcttca tcaccaagga gatgctaggt   360 cccccctccag agacctgcat gttggg                                        386
```

<210> SEQ ID NO 7
<211> LENGTH: 616
<212> TYPE: DNA
<213> ORGANISM: Homo sapiens
<220> FEATURE: -
<223> OTHER INFORMATION: SASA01681F1
<221> NAME/KEY: unsure
<222> LOCATION: 440, 493, 496, 501, 535, 552, 570, 573, 576, 579, 596,
    606, 611
<223> OTHER INFORMATION: a, t, c, g, or other

<400> SEQUENCE: 7

```
actctagagg atcccctgt tctccgctct ggtgggacaa cctgggtgct ggccccaagg     60
ggctcctcca gagagatgtg tgtgacctgg caggtgtaag tggcacctgc agagccaggt   120
tctgcggtga gagaggagga gatgctgtag gtgcctgcca cgctttgcct gaggctggag   180
aaggaggcac cagagacttg ggctggggat ccacccagct cctctcgggt ccacgtcacc   240
accacatcca gagggtaata gccagcaatg tcgcagatga gggtgggcag cagagcttcg   300
tttgccaagc tcagtcgtac tttaggggaa gcttggatgt tgagctggat gatctgctga   360
gctcggtaca gagaggtggt gatctggcaa atgtaggtcc cctcgtcctg tatagtgagg   420
ccgggcaggg tgaaggaggn atccctggcc atgcccagtt gtgcagggct ccaaggtagc   480
ggcctttccg canagnctgc ncctggcccc tgcggttcca agcttgttac acccnaactt   540
gaaccccttg cnccttttgt gcttggccan ttngcnaant tcccaacaat tgattngaag   600
ggttcnaaaa nccccg                                                   616
```

<210> SEQ ID NO 8
<211> LENGTH: 581
<212> TYPE: DNA
<213> ORGANISM: Homo sapiens
<220> FEATURE: -
<223> OTHER INFORMATION: SASA03117F1
<221> NAME/KEY: unsure
<222> LOCATION: 18, 476, 500, 561, 570, 573, 575, 577, 580
<223> OTHER INFORMATION: a, t, c, g, or other

<400> SEQUENCE: 8

```
caggtcgact ctagaggntc ccccctcact atacaggacg aggggaccta catttgccag    60
atcaccacct ctctgtaccg agctcagcag atcatccagc tcaacatcca agcttcccct   120
aaagtacgac tgagcttggc aaacgaagct ctgctgccca ccctcatctg cgacattgct   180
ggctattacc ctctggatgt ggtggtgacg tggacccgag aggagctggg tggatcccca   240
gcccaagtct ctggtgcctc cttctccagc tcaggcaaa gcgtggcagg cacctacagc   300
atctcctcct ctctcaccgc agaacccggc tctgcaggtg ccacttacac ctgccaggtc   360
acacacatct ctctggagga gccccttggg gccagcaccc aggttgtccc accagagcgg   420
agaacagcct tgggagtcat ctttgccagc agtctcttcc ttcttgcact gatgtncctg   480
gggggtttca gagacgggcn agcaacctat agggactttg gggcttgctt tcaggctgaa   540
acgcttggga agacccactt ncctgggccn ganananaan a                       581
```

<210> SEQ ID NO 9
<211> LENGTH: 543
<212> TYPE: DNA
<213> ORGANISM: Homo sapiens
<220> FEATURE: -
<223> OTHER INFORMATION: 2842166T6
<221> NAME/KEY: unsure
<222> LOCATION: 109
<223> OTHER INFORMATION: a, t, c, g, or other

<400> SEQUENCE: 9

```
ccaaaggcat gtggatattt accaatgtca tgtattctga acaaaggcaa aaaatacaaa    60
ttcctaccat taaactggct tggttgttgt ttgggttgga gtagctgtng gggcttgggg   120
aagggtgtcg tttctttcta gtagtctcat gtcgctttag gtcagctggg ctggcttaca   180
cgcgctgtgc ggtcttcatg gagatgggag ctctgtgtgt cagcacagga agtggtctcc   240
cagcgttcag ccttaagcag cccaagtcct gtaggtgctg gctctttggt cttatcctcc   300
atctggacat tctgccttct tcttgtcccc tcacttcttc ctgttctctg ccttggtgca   360
tgagcccagg gtgcacagtg aaggaaggca gaggcctctg cagagccagg cccagtgccc   420
catgagctgg tgccaccttc atgtattttt aacctctgtg acttgactta aaagtccttc   480
tggggagcac gtgaactact cttgtctttc tactcttgcc gtctctgaag ccccaggaac   540
ata                                                                  543
```

<210> SEQ ID NO 10
<211> LENGTH: 247
<212> TYPE: DNA
<213> ORGANISM: Mouse
<220> FEATURE: -
<223> OTHER INFORMATION: 701322243H1
<221> NAME/KEY: unsure
<222> LOCATION: 191, 222, 230
<223> OTHER INFORMATION: a, t, c, g, or other

<400> SEQUENCE: 10

```
aagctcaaca gatcatgcca cttaacatcc tggctccccc caaagtacaa ctgcacttgg    60
caaacaagga tcctctgcct tccctcgtct gcagcattgc cggctactat cctctggatg   120
tgggagtgac gtggattcga gaggagctgg gtggaattcc agcccaagtc tctggtgcct   180
cttctccagc ntcaggcaga gcacgatggg taacttacag cnttgttcan gtgaggctga   240
cccagcc                                                              247
```

<210> SEQ ID NO 11

```
<211> LENGTH: 314
<212> TYPE: DNA
<213> ORGANISM: Rat
<220> FEATURE: -
<223> OTHER INFORMATION: 700294612H1
<221> NAME/KEY: unsure
<222> LOCATION: 8, 22, 70, 71, 72, 77, 78, 82, 86, 96, 130, 143, 155,
      177, 206, 216, 224, 245, 247, 253, 268, 274, 275, 289, 301, 308
<223> OTHER INFORMATION: a, t, c, g, or other

<400> SEQUENCE: 11
tctctggngc ctccttctcc anctcagac agaacatgat gggaacctac agcatttctt        60
ccacggtgan nnccgannce angccncaca ggtgcnactt acacctgcca agttgcccac      120
gtctccctgn aggagcccct ganagtcagc atganggttt tgccaaacac agagcanaga      180
ggagccttgg gagtcatcgt tgccancatc ctcttncttt ttgngctctt gctcctggga      240
cttcntngac agnaagcttc atcatcanag ttcnncaagt ctgtgaggna ctctgagtag      300
ncgctttnct gccc                                                        314

<210> SEQ ID NO 12
<211> LENGTH: 290
<212> TYPE: DNA
<213> ORGANISM: Rat
<220> FEATURE: -
<223> OTHER INFORMATION: 700251347H1
<221> NAME/KEY: unsure
<222> LOCATION: 106
<223> OTHER INFORMATION: a, t, c, g, or other

<400> SEQUENCE: 12
gttttgccaa acacagagca aagaggagcc ttgggagtca tcgttgccag catcctcttc        60 cttttttgcgc tcttgctcct gggacttcat agacagcaag cttcancatc aaagtccacc     120
aagtctgtga ggcactctga gtagccgctt tcctgcctcc gagtacaaag aaaagctctc      180
gtgttctagc tacctaagaa ccctgtgttg aggtgtggga ctgagacggg cctgaaggag      240
gcagcacatt gggagtgagg tactgaccct ggtctgtact agtctctgcc                 290

<210> SEQ ID NO 13
<211> LENGTH: 212
<212> TYPE: DNA
<213> ORGANISM: Rat
<220> FEATURE: -
<223> OTHER INFORMATION: 700255439H1
<221> NAME/KEY: unsure
<222> LOCATION: 129
<223> OTHER INFORMATION: a, t, c, g, or other

<400> SEQUENCE: 13
tcagttgaag ccaagcttcc cacatcctct ttgtttgcca tgaggtgatg tggggtttcc        60
attgtgtctg tcattaccac cgtgtctttc ctaacccagt ctcacagttt atgtatagta      120
gtaagagtng tccttccacc aaaggcatgt gacagattta ccaatctcat gtattctcaa      180
caaaggcgaa aaatacaaat tcctaccaca aa                                    212

<210> SEQ ID NO 14
<211> LENGTH: 225
<212> TYPE: DNA
<213> ORGANISM: Rat
<220> FEATURE: -
<223> OTHER INFORMATION: 700124888H1

<400> SEQUENCE: 14
catgaaggca ccaaataatt tcagggaatg aggggctttg aggataacag gctctcagga        60
```

```
acacgctcca tgccatccca ctctccaatg aaagccctgt acctcccttg ttgattaaga      120
gaaatgagag ttatatggtg agactcccag ggtcccacag aacacttccc cctgcactac      180
ccacttactg tgtgtaagac aaggatgagg caggagggcc tttcc                      225
```

<210> SEQ ID NO 15
<211> LENGTH: 465
<212> TYPE: PRT
<213> ORGANISM: Homo sapiens
<220> FEATURE: -
<223> OTHER INFORMATION: g3169279

<400> SEQUENCE: 15

```
Met Lys Pro Leu Leu Leu Val Ala Val Ala Leu Gly Leu Ala
 1               5                  10                  15

Thr Phe Val Ser Val Ser Ala Gly Pro Glu Ala Ile Glu Cys
            20                  25                  30

Trp Phe Val Glu Asp Ala Gly Gly Gly Leu Ser Lys Lys Pro
            35                  40                  45

Ala Thr Leu Leu Leu Arg His Gly Pro Arg Gly Pro Pro Arg
            50                  55                  60

Pro Asp Leu Asp Pro Lys Leu Tyr Phe Lys Val Asp Asp Pro Ala
            65                  70                  75

Gly Met Leu Leu Ala Ala Phe Arg Arg Tyr Pro Ala Gly Ala Ser
            80                  85                  90

Ala Pro His Cys Glu Met Ser Arg Phe Ile Pro Phe Pro Ala Ser
            95                 100                 105

Ala Lys Trp Ala Arg Ser Leu Ser Pro Glu Gln Asn Cys Pro Arg
           110                 115                 120

Ala Leu Asp Gly Asp Trp Leu Leu Val Ser Val Ser Ser Thr Leu
           125                 130                 135

Phe Ser Leu Ser Ser Leu Leu Arg Pro Gln Pro Glu Pro Leu Arg
           140                 145                 150

Glu Pro Val Val Ile Thr Met Ala Thr Val Val Leu Thr Val Leu
           155                 160                 165

Thr His Asn Pro Ala Pro Arg Val Gln Leu Gly Lys Asp Ala Val
           170                 175                 180

Leu Asp Leu Arg Phe Ala Tyr Ala Pro Ser Ala Leu Glu Gly Ser
           185                 190                 195

Pro Ser Leu Asp Ala Gly Pro Pro Phe Gly Leu Glu Trp Arg
           200                 205                 210

Arg Gln His Arg Gly Lys Gly His Leu Leu Leu Ala Ala Thr Pro
           215                 220                 225

Gly Leu Ala Gly Arg Met Pro Pro Ala Gln Glu Lys Ala Thr Ala
           230                 235                 240

Phe Ala Ala Trp Asp Asp Glu Pro Trp Gly Pro Trp Thr Gly
           245                 250                 255

Asn Gly Thr Phe Trp Leu Pro Ala Val Lys Pro Ser Gln Glu Gly
           260                 265                 270

Val Tyr Leu Gly Thr Val His Leu Pro Tyr Leu Gln Gly Gln Val
           275                 280                 285

Ser Leu Glu Leu Thr Val His Lys Gly Pro Arg Val Ser Leu Thr
           290                 295                 300

Pro Ala Pro Val Val Trp Ala Ala Pro Gly Glu Ala Pro Pro Glu
           305                 310                 315
```

```
Leu Leu Cys Leu Ala Ser His Phe Phe Pro Ala Glu Gly Leu Glu
            320                 325                 330

Val Lys Trp Glu Leu Arg Gly Gly Pro Gly Gly Ser Ser Arg Lys
            335                 340                 345

Val Glu Gly Lys Thr Trp Leu Ser Thr Ile Arg His His Ser Asp
            350                 355                 360

Gly Ser Val Ser Gln Ser Gly His Leu Gln Leu Pro Pro Val Thr
            365                 370                 375

Ala Lys Gln His Gly Val His Tyr Val Cys Arg Val Tyr His Ser
            380                 385                 390

Ser Leu Pro Ala Ser Gly Arg Ser Ala Asp Val Thr Leu Glu Val
            395                 400                 405

Ala Gly Phe Ser Gly Pro Ser Ile Glu Asp Gly Ile Gly Leu Phe
            410                 415                 420

Leu Ser Ala Phe Leu Leu Leu Gly Leu Leu Lys Val Leu Gly Trp
            425                 430                 435

Leu Ala Ala Tyr Trp Thr Ile Pro Glu Val Ser Lys Glu Lys Ala
            440                 445                 450

Thr Ala Ala Ser Leu Thr Ile Pro Arg Asn Ser Lys Lys Ser Gln
            455                 460                 465

<210> SEQ ID NO 16
<211> LENGTH: 402
<212> TYPE: PRT
<213> ORGANISM: Homo sapiens
<220> FEATURE: -
<223> OTHER INFORMATION: 3183699

<400> SEQUENCE: 16

Met Ala Ala Gly Leu Arg Leu Leu Ala Gly Gly Gly Ala Arg
  1               5                  10                  15

Gly Arg Ala Ala Gly Gly Gly Gln Cys Pro Ser Cys Thr Ala Ala
             20                  25                  30

Leu Trp Gly Gly Arg Gly Asp Pro Ser Arg Thr Arg Pro Gly Ala
             35                  40                  45

Arg Ser His Leu Gln Cys Gln Arg Pro Leu Gly Asp Ser Ser Pro
             50                  55                  60

Thr Arg Val Pro Pro Arg Thr Pro Pro Ser Cys Glu Leu Asn Pro
             65                  70                  75

Thr Asn Pro Gln Thr Gly Ser Asp Pro Trp Ser Arg Pro Leu His
             80                  85                  90

Pro Asp Ala Arg Ser Pro Pro Thr Ala Gly Gln Trp Trp Val
             95                 100                 105

Ala Ala Val Gly Thr Pro Gln Tyr Gly Val Thr Ala Leu Leu Gln
            110                 115                 120

Gly Gly Met Gly Thr Glu Gly Thr Ile Thr Ala Ala Val Ala Leu
            125                 130                 135

Ala Val Leu Thr His Thr Pro Thr Leu Arg Ala Arg Val Gly Ser
            140                 145                 150

Pro Ile His Leu His Cys Ala Phe Ala Ala Pro Pro Ser Ser Phe
            155                 160                 165

Val Leu Glu Trp Arg His Gln Asn Arg Gly Ala Gly Arg Val Leu
            170                 175                 180

Leu Ala Tyr Asp Ser Ser Thr Ala Arg Ala Pro Arg Ala His Pro
            185                 190                 195
```

-continued

```
Gly Ala Glu Leu Leu Leu Gly Thr Arg Asp Gly Asp Gly Val Thr
            200                 205                 210
Ala Val Thr Leu Arg Leu Ala Arg Pro Ser Pro Gly Asp Glu Gly
            215                 220                 225
Thr Tyr Ile Cys Ser Val Phe Leu Pro His Gly His Thr Gln Thr
            230                 235                 240
Val Leu Gln Leu His Val Phe Glu Pro Pro Lys Val Thr Leu Ser
            245                 250                 255
Pro Lys Asn Leu Val Val Ala Pro Gly Thr Ser Ala Glu Leu Arg
            260                 265                 270
Cys His Val Ser Gly Phe Tyr Pro Leu Asp Val Thr Val Thr Trp
            275                 280                 285
Gln Arg Arg Ala Gly Gly Ser Gly Thr Ser Gln Ser Pro Arg Asp
            290                 295                 300
Thr Val Met Asp Ser Trp Thr Ser Gly His Arg Gln Ala Ala Asp
            305                 310                 315
Gly Thr Tyr Ser Arg Thr Ala Ala Ala Arg Leu Ile Pro Ala Arg
            320                 325                 330
Pro Gln His His Gly Asp Ile Tyr Ser Cys Val Val Thr His Thr
            335                 340                 345
Ala Leu Ala Lys Pro Met Arg Val Ser Val Arg Leu Leu Leu Ala
            350                 355                 360
Gly Thr Glu Gly Pro His Leu Glu Asp Ile Thr Gly Leu Phe Leu
            365                 370                 375
Val Ala Phe Val Leu Cys Gly Leu Ile Arg Trp Leu Tyr Pro Lys
            380                 385                 390
Ala Ala Arg Pro Lys Glu Glu Thr Lys Lys Ser Gln
            395                 400
```

<210> SEQ ID NO 17
<211> LENGTH: 1482
<212> TYPE: DNA
<213> ORGANISM: Rat
<220> FEATURE: -
<223> OTHER INFORMATION: g207628

<400> SEQUENCE: 17

```
gaattcgggt tccgtctact tcagccgcag cgtctccctg cctgtctcat tgcattctcc      60
agagaggga cggacctcca cttcctcttt cagaaaaatg tctgctccag ctcagccacc     120
tgctgaaggg acagaagggg ctgccccagg tggggtcct cctggtcctc ctcccaatac     180
gaccagtaac agacgattac agcaaaccca ggcacaagtg gaggaggtgg tggacatcat     240
tcgcgtgaat gtggacaagg tcttggagag ggaccagaag ttgtcagagt tggatgaccg     300
agctgacgcc ttgcaggcag gagcgtcagt gtttgagagc agtgctgcca agctaaaaag     360
gaagtattgg tggaaaaact gcaagatgat gatcatgctg ggagctatct gtgccatcat     420
cgtggtagta attgtaatct acatttttac ttgagaatgt gccatccctt ccctgttctc     480
cattgccatc caagctcatg tttcccctct gtttgctctc tcaacaaagt cctccatctt     540
ccgttctcca tcctggccca ggcttctctg tgatccgacc ttccctttt gtgcattcat     600
tcgcactctt cctcaaaact agaaatgctg ctcgtggcac agtcctgaaa gtcactgccc     660
gaagagaaca cccagcacct cctctttacc catttatcat gtgccctgga gcttaaaaga     720
gttgtggcca atggcagagg tgaagtgtct gagaagttag catggctgag gggaagagaa     780
```

-continued

```
aggcatttgt gtccaagaaa ggctggcctt tggcaggagg gaagcaagaa tagttgggaa       840
gtagtagctt gctgccagtg tatatgtata tgtatatgta tatgtatatg tatatgtata       900
tgtatatgta tatattagtt gggaactatg acctgctgtc ctcatttgga actttcctcc       960
cataccaggc ctgtcttggg tcccagaggt ctgtttaaag accaacttca aatcccttt      1020 agaaaaacat caaacttgca ttttgtagct actgttatct gtcagtacaa gattttctgt     1080
gtctttgggg gaactttaca acttttcgct ttgtctctat agccccagga gagaagtact     1140
ttctgatttt aaaaacagca ggacactctt accttcttct agaaggcgtc ccacatgctt     1200
ctgactagaa ggagctacca cctcttcatg tcatctgaag catttgatgt tgttcatgaa     1260
ggcaccaaat aatttcaggg aatgaggggc tttgaggata acaggctctc aggaacacgc    1320
tccatgccat cccactctcc aatgaaagcc ctgtacctcc cttgttgatt aagagaaatg    1380
agagttatat ggtgagactc ccagggtccc acagaacact tccccctgca ctacccactt    1440
actgtgtgta agacaaggat gaggcaggag ggccccgaat tc                        1482
```

TAPASIN-LIKE PROTEIN

This application is a continuation-in-part of U.S. Ser. No. 09/292,097, filed Apr. 14, 1999 now U.S. Pat. No. 6,322,977.

FIELD OF THE INVENTION

This invention relates to a cDNA encoding a tapasin-like protein and to the use of the cDNA, protein, and an antibody binding the protein in the diagnosis, prognosis, treatment and evaluation of therapies for cancers, particularly of the prostate, bladder and lung, and immune response.

BACKGROUND OF THE INVENTION

Phylogenetic relationships among organisms have been demonstrated many times, and studies from a diversity of prokaryotic and eukaryotic organisms suggest a more or less gradual evolution of biochemical and physiological mechanisms and metabolic pathways. Despite different evolutionary pressures, proteins that regulate the cell cycle in yeast, nematode, fly, rat, and man have common chemical or structural features and modulate the same general cellular activity. Comparisons of human gene sequences with those from other organisms where the structure and/or function may be known allow researchers to draw analogies and to develop model systems for testing hypotheses. These model systems are of great importance in developing and testing diagnostic and therapeutic agents for human conditions, diseases and disorders.

Tapasin is a 48-kDa transmembrane glycoprotein. It is found in the endoplasmic reticulum (ER) and displays a cytoplasmic retention signal. Tapasin is a member of the immunoglobulin (Ig) superfamily and is encoded by an major histocompatibility (MHC)-linked gene. The protein plays a critical functional role in MHC class I-restricted antigen processing. Tapasin mediates the interaction between the transporter associated with antigen processing (TAP) and newly synthesized MHC class I molecules by forming complexes with other chaperones such as calnexin and calreticulin. Up to four MHC class I-tapasin complexes bind and present molecules to each TAP molecule. (See Pamer and Cresswell (1998) Annu Rev Immunol 16:323–58; Ortmann et al. (1997) Science 277:1306–9.)

Tapasin is essential for human lymphocyte (HLA) Al, B8, and B4402 antigen presentation. Although tapasin is required for HLA-A2 molecules to bind TAP, its absence affects the overall efficiency of the process of loading HLA-A2 with optimal, stabilizing peptides. With its Ig_MHC binding signature, (Y)xCx(V)xH, tapasin is a necessary cofactor in a multicomponent 'peptide loading complex' where lack of binding results in proteasome-mediated degradation (Lewis et al. (1998) Eur J Immunol 28:3214–20). After analysis of mutant molecules which fail to bind tapasin or TAP, Suh et al. (1999; J Immunol 162:1530–40) also suggested a peptide-editing function for tapasin/TAP in addition to a role in enhancing peptide loading.

Correct antigen presentation to T lymphocytes is important in the infectious disease process. In a study of the mutant MHC class I molecule T134K (in which Thr134 was changed to Lys), Lewis and Elliott (1998; Curr Biol 8:717–20) reported that the point mutation disrupted, directly or indirectly, the interaction between MHC class I molecules and calreticulin. T134K molecules were transported out of the ER as 'empty' MHC class I complexes rather than being retained and degraded and neither bound TAP nor presented viral antigens to T cells.

The discovery of a cDNA encoding a tapasin-like protein provides compositions which are useful in the diagnosis, prognosis, treatment and evaluation of therapies for cancers, particularly of the prostate, bladder and lung, and immune response.

SUMMARY OF THE INVENTION

The present invention is based on the discovery of a cDNA encoding a tapasin-like protein (TLP). The cDNA which encodes the protein, and an antibody which specifically binds the protein are useful in the diagnosis, prognosis, treatment and evaluation of therapies for cancers, particularly of the prostate, bladder and lung, and immune response.

The invention provides an isolated cDNA comprising a nucleic acid sequence of SEQ ID NO:1 which encodes a protein having an amino acid sequence of SEQ ID NO:2. The invention also provides isolated cDNA fragments comprising SEQ ID NOs:3–9 which have about 100% sequence identity with SEQ ID NO:1. The invention additionally provides isolated cDNAs comprising SEQ ID NOs:10–13 which have from about 75% to about 90% nucleotide identity with SEQ ID NO:1. The invention further provides complements of SEQ ID NOs:1 and 3–13.

The invention provides compositions comprising the cDNAs or complements thereof and a labeling moiety or pharmaceutical carrier which may be used in methods of the invention, on a substrate, as probes or therapeutics. The invention also provides a vector containing the cDNA, a host cell containing the vector, and a method for using the cDNA to make tapasin-like protein. The invention additionally provides a transgenic cell line or organism comprising the vector containing a cDNA selected from SEQ ID NO:1 and 3–13. The invention further provides for using a cDNA or the complement thereof in methods of detection, screening, and purification. In one embodiment, the cDNA is a single-stranded RNA or DNA molecule, a peptide nucleic acid, a branched nucleic acid, and the like.

The invention provides a method for using a cDNA to detect differential expression of a nucleic acid in a sample comprising hybridizing a cDNA to the nucleic acids, thereby forming hybridization complexes and comparing hybridization complex formation with at least one standard, wherein the comparison indicates differential expression of the cDNA in the sample. In one aspect, the method further comprises amplifying the nucleic acids of the sample prior to hybridization. In a second aspect, the method is used to diagnose a cancer.

The invention additionally provides a method for using a cDNA or composition of the invention to screen a plurality of molecules or compounds to identify or purify at least one ligand which specifically binds the cDNA or composition, the method comprising combining the cDNA or composition with the molecules or compounds under conditions allowing specific binding, and detecting specific binding to the cDNA or composition, thereby identifying or purifying a ligand which binds the cDNA or composition. In one embodiment, the molecules or compounds are selected from aptamers, DNA molecules, RNA molecules, peptide nucleic acids, artificial chromosome constructions, peptides, transcription factors, repressors, and regulatory molecules.

The invention provides a purified protein or a portion thereof selected from the group consisting of an amino acid sequence of SEQ ID NO:2, a variant of SEQ ID NO:2, an antigenic epitope of SEQ ID NO:2, and a biologically active portion of SEQ ID NO:2. The invention also provides a composition comprising purified protein and a labeling moiety or a pharmaceutical carrier. The invention further provides a method of using a protein to treat a subject with cancer comprising administering to a patient in need of such treatment a composition containing purified protein and a pharmaceutical carrier. The invention still further provides a method for using a protein to screen a library or a plurality of molecules or compounds to identify or purify at least one ligand, the method comprising combining the protein with the molecules or compounds under conditions to allow specific binding and detecting specific binding, thereby identifying or purifying a ligand which specifically binds the protein. In one aspect, the molecules or compounds are selected from DNA molecules, RNA molecules, peptide nucleic acids, peptides, proteins, mimetics, agonists, antagonists, antibodies, immunoglobulins, inhibitors, and drugs. In a second aspect, the ligand is used to treat a subject with a cancer.

The invention provides a method of using a protein having the amino acid sequence of SEQ ID NO:2 to screen a plurality of antibodies to identify and purify an antibody which specifically binds the protein comprising contacting isolated antibodies with the protein under conditions to form an antibody:protein complex, and dissociating the antibody from the protein, thereby obtaining purified antibody which specifically binds the protein.

The invention also provides a method of using a protein having the amino acid sequence of SEQ ID NO:2 to prepare and purify polyclonal and monoclonal antibodies which specifically bind the protein. The method for using the protein to prepare a polyclonal antibody comprises immunizing a animal with protein under conditions to elicit an antibody response, isolating animal antibodies, attaching the protein to a substrate, contacting the substrate with isolated antibodies under conditions to allow specific binding to the protein, dissociating the antibodies from the protein, thereby obtaining purified polyclonal antibodies. The method for using the protein to prepare monoclonal antibodies comprises immunizing an animal with a protein under conditions to elicit an antibody response, isolating antibody producing cells from the animal, fusing the antibody producing cells with immortalized cells in culture to form monoclonal antibody producing hybridoma cells, culturing the hybridoma cells, and isolating from culture monoclonal antibodies which specifically bind the protein.

The invention provides purified polyclonal and monoclonal antibodies which bind specifically to a tapasin-like protein. The invention also provides a method for using an antibody to detect expression of a protein in a sample, the method comprising combining the antibody with a sample under conditions which allow the formation of antibody:protein complexes; and detecting complex formation, wherein complex formation indicates expression of the protein in the sample. In one aspect, the amount of complex formation when compared to standards is diagnostic of cancer.

The invention provides a method for inserting a heterologous marker gene into the genomic DNA of a mammal to disrupt the expression of an endogenous polynucleotide. The invention also provides a method for using a cDNA to produce a model system, the method comprising constructing a vector containing a DNA selected from SEQ ID NOs:1 and 3–13, transforming the vector into an embryonic stem cell, selecting a transformed embryonic stem cell, microinjecting the transformed embryonic stem cell into a blastocyst, thereby forming a chimeric blastocyst, transferring the chimeric blastocyst into a pseudopregnant dam, wherein the dam gives birth to a chimeric offspring containing the cDNA in its germ line, and breeding the chimeric mammal to produce a homozygous, model system.

BRIEF DESCRIPTION OF THE FIGURES AND TABLE

FIGS. 1A–1E show the cDNA (SEQ ID NO:1) encoding the amino acid sequence (SEQ ID NO:2) of the protein. The alignment was produced using MACDNASIS PRO software (Hitachi Software Engineering, South San Francisco Calif.).

FIGS. 2A–2F show the alignment between SEQ ID NO:1 and each of SEQ ID NOs:3–13 as produced using Phrap (Phil Green, University of Washington, Seattle Wash.).

Figure 2A:
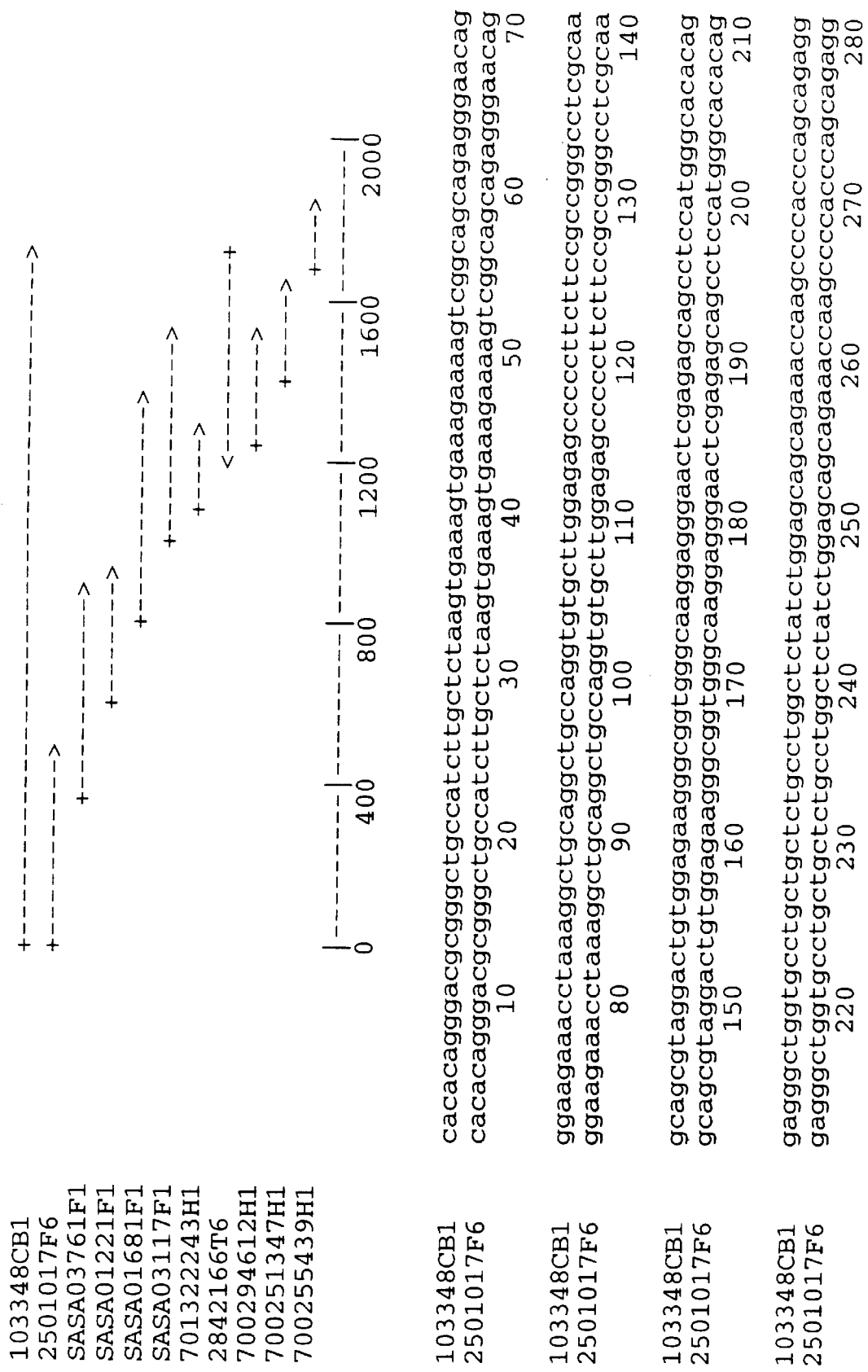

FIGS. 3A and 3B demonstrate the chemical and structural similarity between SEQ ID NO:2, mouse tapasin (g3169279, SEQ ID NO:15), and chicken tapasin (g3183699; SEQ ID NO:16) as produced using the MEGALIGN program (DNASTAR, Madison Wis.).

DESCRIPTION OF THE INVENTION

It is understood that this invention is not limited to the particular machines, materials and methods described. It is also to be understood that the terminology used herein is for the purpose of describing particular embodiments only and is not intended to limit the scope of the present invention which will be limited only by the appended claims. As used herein, the singular forms "a" "an," and "the" include plural reference unless the context clearly dictates otherwise. For example, a reference to "a host cell" includes a plurality of such host cells known to those skilled in the art.

Unless defined otherwise, all technical and scientific terms used herein have the same meanings as commonly understood by one of ordinary skill in the art to which this invention belongs. All publications mentioned herein are cited for the purpose of describing and disclosing the cell lines, protocols, reagents and vectors which are reported in the publications and which might be used in connection with the invention. Nothing herein is to be construed as an admission that the invention is not entitled to antedate such disclosure by virtue of prior invention.

Definitions

"TLP" refers to a purified protein obtained from any mammalian species, including murine, bovine, ovine, porcine, rodent, canine, simian, and preferably the human species, and from any source, whether natural, synthetic, semi-synthetic, or recombinant.

"Array" refers to an ordered arrangement of at least two cDNAs or antibodies on a substrate. At least one of the cDNAs or antibodies represents a control or standard, and the other, a cDNA or antibody of diagnostic or therapeutic interest. The arrangement of two to about 40,000 cDNAs or of two to about 40,000 monoclonal or polyclonal antibodies on the substrate assures that the size and signal intensity of each labeled hybridization complex, formed between each cDNA and at least one nucleic acid, or antibody:protein complex, formed between each antibody and at least one protein to which the antibody specifically binds, is individually distinguishable.

"Cancer" refers to cell proliferative conditions, diseases, disorders, or syndromes and specifically to human cancers of the prostate, bladder and lung, in which tapasin-like protein and its encoding cDNAs are differentially expressed. Differential expression of tapasin-like protein is manifest by up-regulation or increase at onset of cancer. The specific cancers which may be diagnosed using tapasin-like protein and its encoding cDNA include adenofibromatous hyperplasia of the prostate, transitional cell carcinoma of the bladder, and adenocarcinoma, squamous cell carcinoma, and endobronchial carcinoid tumors of the lung.

The "complement" of a cDNA of the Sequence Listing refers to a nucleic acid molecule which is completely complementary to the cDNA over its full length and which will hybridize to the cDNA or an mRNA under conditions of maximal stringency.

"cDNA" refers to an isolated polynucleotide, nucleic acid molecule, or any fragment or complement thereof. It may have originated recombinantly or synthetically, may be double-stranded or single-stranded, represents coding and noncoding 3' or 5' sequence, and generally lacks introns. cDNAs can be labeled with reporter molecules for use in hybridization reactions including Southern, northern, in situ, dot blot, array, and like technologies or in screening assays.

A "composition" refers to apolynucleotide and a labeling moiety or pharmaceutical carrier, a purified protein and a labeling moiety or a pharmaceutical carrier, an antibody and a labeling moiety, and the like.

"Derivative" refers to a cDNA or a protein that has been subjected to a chemical modification. Derivatization of a cDNA can involve substitution of a nontraditional base such as queosine or of an analog such as hypoxanthine. Derivatization of a protein involves the replacement of a hydrogen by an acetyl, acyl, alkyl, amino, formyl, or morpholino group. Derivative molecules retain the biological activities of the naturally occurring molecules but may confer advantages such as longer lifespan or enhanced activity.

"Differential expression" refers to an increased or up-regulated or a decreased or down-regulated expression as detected by presence, absence or at least two-fold change in the amount or abundance of a transcribed messenger RNA or translated protein in a sample.

"Fragment" refers to a chain of consecutive nucleotides from about 50 to about 5000 base pairs in length. Fragments may be used in PCR or hybridization technologies to identify related nucleic acid molecules and in binding assays to screen for a ligand. Such ligands are useful as therapeutics to regulate replication, transcription or translation.

A "hybridization complex" is formed between a cDNA and a nucleic acid of a sample when the purines of one molecule hydrogen bond with the pyrimidines of the complementary molecule, e.g., 5'-A-G-T-C-3' base pairs with 3'-T-C-A-G-5'. Hybridization conditions, degree of complementarity and the use of nucleotide analogs affect the efficiency and stringency of hybridization reactions.

"Labeling moiety" refers to any visible or radioactive label than can be attached to or incorporated into a cDNA or protein. Visible labels include but are not limited to anthocyanins, green fluorescent protein (GFP), β glucuronidase, luciferase, Cy3 and Cy5, and the like. Radioactive labels include radioactive forms of hydrogen, iodine, phosphorous, sulfur, and the like.

"Ligand" refers to any agent, molecule, or compound which will bind specifically to a polynucleotide or to an epitope of a protein. Such ligands stabilize or modulate the activity of polynucleotides or proteins and may be composed of inorganic and/or organic substances including minerals, cofactors, nucleic acids, proteins, carbohydrates, fats, and lipids.

"Oligonucleotide" refers a single-stranded molecule from about 18 to about 60 nucleotides in length which may be used in hybridization or amplification technologies or in regulation of replication, transcription or translation. Equivalent terms are amplimer, primer, and oligomer.

An "oligopeptide" is an amino acid sequence from about five residues to about 15 residues that is used as part of a fusion protein to produce an antibody.

"Portion" refers to any part of a protein used for any purpose; but especially, to a biologically active motif or domain to be used for screening purposes or to an epitope for the production of antibodies.

"Post-translational modification" of a protein can involve lipidation, glycosylation, phosphorylation, acetylation, racemization, proteolytic cleavage, and the like. These processes may occur synthetically or biochemically. Biochemical modifications will vary by cellular location, cell type, pH, enzymatic milieu, and the like.

"Protein" refers to a polypeptide or any portion thereof. A "portion" of a protein refers to that length of amino acid sequence which would retain at least one biological activity, a domain identified by PFAM or PRINTS analysis or an antigenic epitope of the protein identified using Kyte-Doolittle algorithms of the PROTEAN program (DNASTAR).

"Purified" refers to any molecule or compound that is separated from its natural environment and is from about 60% free to about 90% free from other components with which it is naturally associated.

"Sample" is used in its broadest sense as containing nucleic acids, proteins, antibodies, and the like. A sample may comprise a bodily fluid; the soluble fraction of a cell preparation, or an aliquot of media in which cells were grown; a chromosome, an organelle, or membrane isolated or extracted from a cell; genomic DNA, RNA, or cDNA in solution or bound to a substrate; a cell; a tissue; a tissue print; a fingerprint, buccal cells, skin, or hair; and the like.

"Similarity" refers to the quantification (usually percentage) of nucleotide or residue matches between at least two sequences aligned using a standard algorithm such as Smith-Waterman alignment (Smith and Waterman (1981) J Mol Biol 147:195–197) or BLAST2 (Altschul et al. (1997) Nucleic Acids Res 25:3389–3402). BLAST2 may be used in a reproducible way to insert gaps in one of the sequences in order to optimize alignment and to achieve a more meaningful comparison between them. Particularly in proteins, similarity is greater than identity in that conservative substitutions (for example, valine for leucine or isoleucine) are counted in calculating the reported percentage. Substitutions which are considered to be conservative are well known in the art.

"Specific binding" refers to a special and precise interaction between two molecules which is dependent upon their structure, particularly their molecular side groups. For example, the intercalation of a regulatory protein into the major groove of a DNA molecule or the binding between an epitope of a protein and an agonist, antagonist, or antibody.

"Substrate" refers to any rigid or semi-rigid support to which cDNAs or proteins are bound and includes membranes, filters, chips, slides, wafers, fibers, magnetic or nonmagnetic beads, gels, capillaries or other tubing, plates, polymers, and microparticles with a variety of surface forms including wells, trenches, pins, channels and pores.

A "transcript image" is a profile of gene transcription activity in a particular tissue at a particular time.

"Variant" refers to molecules that are recognized variations of a cDNA or a protein encoded by the cDNA. Splice variants may be determined by BLAST score, wherein the score is at least 100, and most preferably at least 400. Allelic variants have a high percent identity to the cDNAs and may differ by about three bases per hundred bases. "Single nucleotide polymorphism" (SNP) refers to a change in a single base as a result of a substitution, insertion or deletion. The change may be conservative (purine for purine) or non-conservative (purine to pyrimidine) and may or may not result in a change in an encoded amino acid or its secondary, tertiary, or quaternary structure.

The Invention

The invention is based on the discovery of a tapasin-like protein (TLP) and its encoding cDNA, first described in U.S. Ser. No. 09/292,097, filed Apr. 14, 1999, and incorporated herein in its entirety. The cDNA, or fragments thereof, the amino acid sequence, or portions thereof, and an antibody which specifically binds the protein may be used as compositions in the diagnosis, prognosis, treatment and evaluation of therapies for cancers, particularly of the prostate, bladder and lung, and immune response.

cDNAs encoding the protein of the present invention were identified by BLAST analysis. Incyte clone 700124888 (SEQ ID NO:14) from the rat cerebral hemisphere tissue library (RABHNOT01) which aligns with rat vesicle associated membrane protein (VAMP-1; g207628). VAMP-1 (SEQ ID NO:17) was used to identify related VAMP and tapasin-like cDNAs in the LIFESEQ database (Incyte Genomics, Palo Alto Calif.). These cDNAs contain the nucleotide sequences presented in SEQ ID NOs:3–9, each of which has ~100% homology with and contributed to the assembly of the full length consensus sequence, SEQ ID NO:1, shown in FIGS. 1A–1E.

The fragments comprising SEQ ID NO:10 from mouse and SEQ ID NO:11–13 from rat, were identified using either SEQ ID NO:1 or one of the Incyte clones, SEQ ID NOs:3–9. FIGS. 2A–2F and the table below show the alignment and identities among SEQ ID NOs:1 and 3–13. Column 1 of the table SEQ ID; column 2, Incyte clone number; column 3, length of the nucleotide sequence; column 4, the tissue source; column 5, the library associated with the cDNA; column 6, the alignment or region of overlap between each cDNA and SEQ ID NO:1; and column 8, the % identity of each sequence with SEQ ID NO:1.

prostate, bladder and lung. When used in a tissue specific assay with biopsied tissue from prostate, bladder or lung, the cDNA encoding the tapasin-like protein is diagnostic for adenofibromatous hyperplasia of the prostate, transitional cell carcinoma of the bladder, and adenocarcinoma, squamous cell carcinoma, and endobronchial carcinoid tumors of the lung. In prostate, SEQ ID NO:1 distinguishes adenofibromatous hyperplasia from benign prostatic hypertrophy and prostate intraepithelial neoplasia. In lung, SEQ ID NO:1 distinguishes lung cancer from asthma, chronic obstructive pulmonary disease, pneumonitis and emphysema.

TLP comprising the amino acid sequence of SEQ ID NO:2 is 468 amino acids in length and has a signal peptide from residue M1 to residue E20, a potential transmembrane domain from residue L408 to residue L426, nine casein kinase II phosphorylation sites at residues S53, S74, S116, T165, T187, T274, T336, S388, and S447; six protein kinase C phosphorylation sites at residues T135, T161, T184, S303, S354, and T461; and an Ig_MHC signature from residue Y380 to residue H386. FIGS. 3A and 3B demonstrate the chemical and structural similarity among TLP, mouse tapasin (SEQ ID NO: 15), and chicken tapasin (SEQ ID NO:16). Of particular note are the conserved cysteine residues 39, 122, 321, 382; the shared Ig_MHC signature, Y380–H386; the conserved residues, G205, L210, E226–R228, Q230, G233, G235, D265, L270, and E278–Y281, of the Ig binding domain predicted by HMM to extend from G205–I285 and the conserved residues, L319, C321, Y327, P328, V360, W335, R337, G342, S354, and R356, of the Ig binding domain predicted by HMM to extend from L316–S358. The amino acids of SEQ ID NO:2, from residue G17 to residue V33 or from residue L110 to residue Y127 are particularly useful epitopes for antibody production.

It will be appreciated by those skilled in the art that as a result of the degeneracy of the genetic code, a multitude of

| SEQ ID | CLONE | LENGTH | SOURCE | LIBRARY | ALIGNMENT | % IDENTITY |
|---|---|---|---|---|---|---|
| 1 | 103348CB1 | 1764 | Human | BMARNOT02 | 1–1764 | consensus |
| 3 | 103348H1 | 258 | Human | BMARNOT02 | 1038–1276 | ~100 |
| 4 | 2501017F6 | 533 | Human | ADRETUT05 | 1–535 | ~100 |
| 5 | SASA03761F1 | 593 | Human | (SHOTGUN) | 404–1001 | ~100 |
| 6 | SASA01221F1 | 386 | Human | (SHOTGUN) | 636–1025 | ~100 |
| 7 | SASA01681F1 | 616 | Human | (SHOTGUN) | 830–1450 | ~100 |
| 8 | SASA03117F1 | 581 | Human | (SHOTGUN) | 1003–1588 | ~100 |
| 9 | 2842166T6 | 543 | Human | DRGLNOT01 | 1237–1797 | ~100 |
| 10 | 701322243H1 | 247 | Mus musculus | MOAPUNT01 | 1082–1331 | 81 |
| 11 | 700294612H1 | 314 | Rattus norvegicus | RABFNOT02 | 1403–1490 | 75 |
| 12 | 700251347H1 | 290 | Rattus norvegicus | RABMNOT01 | 1403–1497 | 80 |
| 13 | 700255439H1 | 212 | Rattus norvegicus | RABMNOT02 | 1764–1694 | 90 |

Any of the cDNAs of SEQ ID NOs:1 and 3–13 may be used in hybridization and amplification technologies to identify and distinguish among SEQ ID NO:1 and related molecules in a sample. The cDNAs may also be used in screening methods to identify ligands which affect expression of the endogenous gene. The cDNAs further may b used to produce transgenic cell lines or organisms which are model systems for the initiation, development and treatment of cancers and upon which the toxicity and efficacy of potential therapeutic treatments may be tested. Toxicology studies, clinical trials, and subject/patient treatment profiles may be performed and monitored using the cDNAs, proteins, antibodies and molecules and compounds identified using the cDNAs and proteins of the present invention.

The transcript image for SEQ ID NO:1, EXAMPLE XIII, shows differential expression of mRNAs in cancers of the cDNAs encoding TLP, some bearing minimal similarity to the cDNAs of any known and naturally occurring gene, may be produced. Thus, the invention contemplates each and every possible variation of cDNA that could be made by selecting combinations based on possible codon choices. These combinations are made in accordance with the standard triplet genetic code as applied to the polynucleotide encoding naturally occurring tapasin-like protein, and all such variations are to be considered as being specifically disclosed.

Characterization and Use of the Invention cDNA libraries

In a particular embodiment disclosed herein, mRNA is isolated from cells and tissues using methods which are well known to those skilled in the art and used to prepare the cDNA libraries. The Incyte cDNAs were isolated from cDNA libraries prepared as described in the EXAMPLES. The consensus sequences are chemically and/or electronically assembled from fragments including Incyte cDNAs and extension and/or shotgun sequences using computer programs such as PHRAP (P Green, University of Washington, Seattle Wash.), and the AUTOASSEMBLER application (ABI). After verification of the 5' and 3' sequence, at least one of the representative cDNAs which encode TLP has been designated a reagent. These cDNAs are also used in the construction of human microarrays and are represented among the sequences on the LifeGEM 1 array (Incyte Genomics).

Sequencing

Methods for sequencing nucleic acids are well known in the art and may be used to practice any of the embodiments of the invention. These methods employ enzymes such as the Klenow fragment of DNA polymerase I, SEQUENASE, Taq DNA polymerase and thermostable T7 DNA polymerase (Amersham Pharmacia Biotech (APB), Piscataway N.J.), or combinations of polymerases and proofreading exonucleases such as those found in the ELONGASE amplification system (Life Technologies, Gaithersburg Md.). Preferably, sequence preparation is automated with machines such as the MICROLAB 2200 system (Hamilton, Reno Nev.) and the DNA ENGINE thermal cycler (MJ Research, Watertown Me.). Machines commonly used for sequencing include the ABI PRISM 3700, 377 or 373 DNA sequencing systems (ABI), the MEGABACE 1000 DNA sequencing system (APB), and the like. The sequences may be analyzed using a variety of algorithms well known in the art and described in Ausubel et al. (1997; *Short Protocols in Molecular Biology*, John Wiley & Sons, New York N.Y., unit 7.7) and in Meyers (1995; *Molecular Biology and Biotechnology*, Wiley VCH, New York N.Y., pp. 856–853).

Shotgun sequencing may also be used to complete the sequence of a particular cloned insert of interest. Shotgun strategy involves randomly breaking the original insert into segments of various sizes and cloning these fragments into vectors. The fragments are sequenced and reassembled using overlapping ends until the entire sequence of the original insert is known. Shotgun sequencing methods are well known in the art and use thermostable DNA polymerases, heat-labile DNA polymerases, and primers chosen from representative regions flanking the cDNAs of interest. Incomplete assembled sequences are inspected for identity using various algorithms or programs such as CONSED (Gordon (1998) Genome Res 8:195–202) which are well known in the art. Contaminating sequences, including vector or chimeric sequences, or deleted sequences can be removed or restored, respectively, organizing the incomplete assembled sequences into finished sequences.

Extension of the Nucleic Acid Sequence of a cDNA

The sequences of the invention may be extended using various PCR-based methods known in the art. For example, the XL-PCR kit (ABI), nested primers, and commercially available cDNA or genomic DNA libraries may be used to extend the nucleic acid sequence. For all PCR-based methods, primers may be designed using commercially available software to be about 22 to 30 nucleotides in length, to have a GC content of about 50% or more, and to anneal to a target molecule at temperatures from about 55 C to about 68 C. When extending a sequence to recover regulatory elements, it is preferable to use genomic, rather than cDNA libraries.

Hybridization

The cDNA and fragments thereof can be used in hybridization technologies for various purposes. A probe may be designed or derived from unique regions such as the 5' regulatory region or from a nonconserved region (i.e., 5' or 3' of the nucleotides encoding the conserved catalytic domain of the protein) and used in protocols to identify naturally occurring molecules encoding TLP, allelic variants, or related molecules. The probe may be DNA or RNA, may be single-stranded, and should have at least 50% sequence identity to SEQ ID NOs:1 and 3–13. Hybridization probes may be produced using oligolabeling, nick translation, end-labeling, or PCR amplification in the presence of a reporter molecule. A vector containing the cDNA or a fragment thereof may be used to produce an mRNA probe in vitro by addition of an RNA polymerase and labeled nucleotides. These procedures may be conducted using commercially available kits.

The stringency of hybridization is determined by G+C content of the probe, salt concentration, and temperature. In particular, stringency can be increased by reducing the concentration of salt or raising the hybridization temperature. Hybridization can be performed at low stringency with buffers, such as 5×SSC with 1% sodium dodecyl sulfate (SDS) at 60 C, which permits the formation of a hybridization complex between nucleic acid sequences that contain some mismatches. Subsequent washes are performed at higher stringency with buffers such as 0.2×SSC with 0.1% SDS at either 45 C (medium stringency) or 68 C (high stringency). At high stringency, hybridization complexes will remain stable only where the nucleic acids are completely complementary. In some membrane-based hybridizations, preferably 35% or most preferably 50%, formamide can be added to the hybridization solution to reduce the temperature at which hybridization is performed, and background signals can be reduced by the use of detergents such as Sarkosyl or TRITON X-100 (Sigma-Aldrich, St Louis Mo.) and a blocking agent such as denatured salmon sperm DNA. Selection of components and conditions for hybridization are well known to those skilled in the art and are reviewed in Ausubel (supra) and Sambrook et al. (1989) *Molecular Cloning, A Laboratory Manual*, Cold Spring Harbor Press, Plainview N.Y.

Arrays incorporating cDNAs or antibodies may be prepared and analyzed using methods well known in the art. Oligonucleotides or cDNAs may be used as hybridization probes or targets to monitor the expression level of large numbers of genes simultaneously or to identify genetic variants, mutations, and single nucleotide polymorphisms. Monoclonal or polyclonal antibodies may be used to detect or quantify expression of a protein in a sample. Such arrays may be used to determine gene function; to understand the genetic basis of a condition, disease, or disorder; to diagnose a condition, disease, or disorder; and to develop and monitor the activities of therapeutic agents. (See, e.g., Brennan et al. (1995) U.S. Pat. No. 5,474,796; Schena et al. (1996) Proc Natl Acad Sci 93:10614–10619; Heller et al. (1997) Proc Natl Acad Sci 94:2150–2155; Heller et al. (1997) U.S. Pat. No. 5,605,662; and deWildt et al. (2000) Nature Biotechnol 18:989–994.)

Hybridization probes are also useful in mapping the naturally occurring genomic sequence. The probes may be hybridized to a particular chromosome, a specific region of a chromosome, or an artificial chromosome construction. Such constructions include human artificial chromosomes (HAC), yeast artificial chromosomes (YAC), bacterial artificial chromosomes (BAC), bacterial P1 constructions, or the cDNAs of libraries made from single chromosomes.

Expression

Any one of a multitude of cDNAs encoding TLP may be cloned into a vector and used to express the protein, or portions thereof, in host cells. The nucleic acid sequence can be engineered by such methods as DNA shuffling, as described in U.S. Pat. No. 5,830,721, and site-directed mutagenesis to create new restriction sites, alter glycosylation patterns, change codon preference to increase expression in a particular host, produce splice variants, extend half-life, and the like. The expression vector may contain transcriptional and translational control elements (promoters, enhancers, specific initiation signals, and polyadenylated 3' sequence) from various sources which have been selected for their efficiency in a particular host. The vector, cDNA, and regulatory elements are combined using in vitro recombinant DNA techniques, synthetic techniques, and/or in vivo genetic recombination techniques well known in the art and described in Sambrook (supra, ch. 4, 8, 16 and 17).

A variety of host systems may be transformed with an expression vector. These include, but are not limited to, bacteria transformed with recombinant bacteriophage, plasmid, or cosmid DNA expression vectors; yeast transformed with yeast expression vectors; insect cell systems transformed with baculovirus expression vectors; plant cell systems transformed with expression vectors containing viral and/or bacterial elements, or animal cell systems (Ausubel supra, unit 16). For example, an adenovirus transcription/translation complex may be utilized in mammalian cells. After sequences are ligated into the E1 or E3 region of the viral genome, the infective virus is used to transform and express the protein in host cells. The Rous sarcoma virus enhancer or SV40 or EBV-based vectors may also be used for high-level protein expression.

Routine cloning, subcloning, and propagation of cDNAs can be achieved using the multifunctional PBLUESCRIPT vector (Stratagene, La Jolla Calif.) or PSPORT1 plasmid (Life Technologies). Introduction of a nucleic acid sequence into the multiple cloning site of these vectors disrupts the lacZ gene and allows calorimetric screening for transformed bacteria. In addition, these vectors may be useful for in vitro transcription, dideoxy sequencing, single strand rescue with helper phage, and creation of nested deletions in the cloned sequence.

For long term production of recombinant proteins, the vector can be stably transformed into cell lines along with a selectable or visible marker gene on the same or on a separate vector. After transformation, cells are allowed to grow for about 1 to 2 days in enriched media and then are transferred to selective media. Selectable markers, antimetabolite, antibiotic, or herbicide resistance genes, confer resistance to the relevant selective agent and allow growth and recovery of cells which successfully express the introduced sequences. Resistant clones identified either by survival on selective media or by the expression of visible markers may be propagated using culture techniques. Visible markers are also used to estimate the amount of protein expressed by the introduced genes. Verification that the host cell contains the desired cDNA is based on DNA-DNA or DNA-RNA hybridizations or PCR amplification techniques.

The host cell may be chosen for its ability to modify a recombinant protein in a desired fashion. Such modifications include acetylation, carboxylation, glycosylation, phosphorylation, lipidation, acylation and the like. Post-translational processing which cleaves a "prepro" form may also be used to specify protein targeting, folding, and/or activity. Different host cells available from the ATCC (Manassas Va.) which have specific cellular machinery and characteristic mechanisms for post-translational activities may be chosen to ensure the correct modification and processing of the recombinant protein.

Recovery of Proteins from Cell Culture

Heterologous moieties engineered into a vector for ease of purification include glutathione S-transferase (GST), 6xHis, FLAG, MYC, and the like. GST and 6xHis are purified using commercially available affinity matrices such as immobilized glutathione and metal-chelate resins, respectively. FLAG and MYC are purified using commercially available monoclonal and polyclonal antibodies. For ease of separation following purification, a sequence encoding a proteolytic cleavage site may be part of the vector located between the protein and the heterologous moiety. Methods for recombinant protein expression and purification are discussed in Ausubel (supra, unit 16) and are commercially available.

Chemical Synthesis of Peptides

Proteins or portions thereof may be produced not only by recombinant methods, but also by using chemical methods well known in the art. Solid phase peptide synthesis may be carried out in a batchwise or continuous flow process which sequentially adds α-amino- and side chain-protected amino acid residues to an insoluble polymeric support via a linker group. A linker group such as methylamine-derivatized polyethylene glycol is attached to poly(styrene-co-divinylbenzene) to form the support resin. The amino acid residues are N-α-protected by acid labile Boc (t-butyloxycarbonyl) or base-labile Fmoc (9-fluorenylmethoxycarbonyl). The carboxyl group of the protected amino acid is coupled to the amine of the linker group to anchor the residue to the solid phase support resin. Trifluoroacetic acid or piperidine are used to remove the protecting group in the case of Boc or Fmoc, respectively. Each additional amino acid is added to the anchored residue using a coupling agent or pre-activated amino acid derivative, and the resin is washed. The full length peptide is synthesized by sequential deprotection, coupling of derivitized amino acids, and washing with dichloromethane and/or N, N-dimethylformamide. The peptide is cleaved between the peptide carboxy terminus and the linker group to yield a peptide acid or amide. These processes are described in the Novabiochem 1997/98 Catalog and Peptide Synthesis Handbook (San Diego Calif. pp. S1–S20). Automated synthesis may also be carried out on machines such as the ABI 431A peptide synthesizer (ABI). A protein or portion thereof may be purified by preparative high performance liquid chromatography and its composition confirmed by amino acid analysis or by sequencing (Creighton (1984) *Proteins, Structures and Molecular Properties*, WH Freeman, New York N.Y.).

Preparation and Screening of Antibodies

Various hosts including, but not limited to, goats, rabbits, rats, mice, and human cell lines may be immunized by injection with TLP or any portion thereof. Adjuvants such as Freund's, mineral gels, and surface active substances such as lysolecithin, pluronic polyols, polyanions, peptides, oil emulsions, keyhole limpet hemacyanin (KLH), and dinitrophenol may be used to increase immunological response. The oligopeptide, peptide, or portion of protein used to induce antibodies should consist of at least about five amino acids, more preferably ten amino acids, which are identical to a portion of the natural protein. Oligopeptides may be fused with proteins such as KLH in order to produce antibodies to the chimeric molecule.

Monoclonal antibodies may be prepared using any technique which provides for the production of antibodies by continuous cell lines in culture. These include, but are not limited to, the hybridoma technique, the human B-cell hybridoma technique, and the EBV-hybridoma technique.

(See, e.g., Kohler et al. (1975) Nature 256:495–497; Kozbor et al. (1985) J. Immunol Methods 81:31–42; Cote et al. (1983) Proc Natl Acad Sci 80:2026–2030; and Cole et al. (1984) Mol Cell Biol 62:109–120.)

Alternatively, techniques described for antibody production may be adapted, using methods known in the art, to produce epitope-specific, single chain antibodies. Antibody fragments which contain specific binding sites for epitopes of the protein may also be generated. For example, such fragments include, but are not limited to, F(ab')2 fragments produced by pepsin digestion of the antibody molecule and Fab fragments generated by reducing the disulfide bridges of the F(ab)2 fragments. Alternatively, Fab expression libraries may be constructed to allow rapid and easy identification of monoclonal Fab fragments with the desired specificity. (See, e.g., Huse et al. (1989) Science 246:1275–1281.)

The tapasin-like protein, or a portion thereof, may be used in screening assays of phagemid or B-lymphocyte immunoglobulin libraries to identify antibodies having the desired specificity. Numerous protocols for competitive binding or immunoassays using either polyclonal or monoclonal antibodies with established specificities are well known in the art. Such immunoassays typically involve the measurement of complex formation between the protein and its specific antibody. A two-site, monoclonal-based immunoassay utilizing monoclonal antibodies reactive to two non-interfering epitopes is preferred, but a competitive binding assay may also be employed (Pound (1998) *Immunochemical Protocols*, Humana Press, Totowa N.J.).

Labeling of Molecules for Assay

A wide variety of reporter molecules and conjugation techniques are known by those skilled in the art and may be used in various nucleic acid, amino acid, and antibody assays. Synthesis of labeled molecules may be achieved using commercially available kits (Promega, Madison Wis.) for incorporation of a labeled nucleotide such as $^{32}$P-dCTP (APB), Cy3-dCTP or Cy5-dCTP (Operon Technologies, Alameda Calif.), or amino acid such as $^{35}$S-methionine (APB). Nucleotides and amino acids may be directly labeled with a variety of substances including fluorescent, chemiluminescent, or chromogenic agents, and the like, by chemical conjugation to amines, thiols and other groups present in the molecules using reagents such as BIODIPY or FITC (Molecular Probes, Eugene Oreg.).

Diagnostics

Nucleic Acid Assays

The cDNAs, fragments, oligonucleotides, complementary RNA and DNA molecules, and PNAs may be used to detect and quantify differential gene expression for diagnostic purposes. Cancers associated with differential expression of SEQ ID NO:1 include adenofibromatous hyperplasia of the prostate, transitional cell carcinoma of the bladder, and adenocarcinoma, squamous cell carcinoma, and endobronchial carcinoid tumors of the lung. In prostate, SEQ ID NO:1 distinguishes adenofibromatous hyperplasia from benign prostatic hypertrophy and prostate intraepithelial neoplasia. In lung, SEQ ID NO:1 distinguishes lung cancer from asthma, chronic obstructive pulmonary disease, pneumonitis and emphysema. The diagnostic assay may use hybridization or quantitative PCR to compare gene expression in a biological sample from a patient to standard samples in order to detect differential gene expression. Qualitative and quantitative methods for this comparison are commercially available and well known in the art.

For example, the cDNA or probe may be labeled by standard methods and added to a biological sample from a patient under conditions for the formation of hybridization complexes. After an incubation period, the sample is washed and the amount of label (or signal) associated with hybridization complexes, is quantified and compared with a standard value. If complex formation in the patient sample is significantly altered (higher or lower) in comparison to either a normal or disease standard, then differential expression indicates the presence of a disorder.

In order to provide standards for establishing differential expression, normal and disease expression profiles are established. This is accomplished by combining a sample taken from normal subjects, either animal or human, with a cDNA under conditions for hybridization to occur. Standard hybridization complexes may be quantified by comparing the values obtained using normal subjects with values from an experiment in which a known amount of a purified sequence is used. Standard values obtained in this manner may be compared with values obtained from samples from patients who were diagnosed with a particular condition, disease, or disorder. Deviation from standard values toward those associated with a particular disorder is used to diagnose that disorder.

Such assays may also be used to evaluate the efficacy of a particular therapeutic treatment regimen in animal studies or in clinical trials or to monitor the treatment of an individual patient. Once the presence of a condition is established and a treatment protocol is initiated, diagnostic assays may be repeated on a regular basis to determine if the level of expression in the patient begins to approximate that which is observed in a normal subject. The results obtained from successive assays may be used to show the efficacy of treatment over a period ranging from several days to years.

Protein Assays

Detection and quantification of a protein using either labeled amino acids or polyclonal or monoclonal antibodies which specifically bind the protein are known in the art. Examples of such techniques include two-dimensional polyacrylamide gel electrophoresis, enzyme-linked immunosorbent assays (ELISAs), radioimmunoassays (RIAs), and fluorescence activated cell sorting (FACS). These assays and their quantitation against purified, labeled standards are well known in the art (Ausubel, supra, unit 10.1–10.6).

Recently, antibody arrays have allowed the development of techniques for high-throughput screening of recombinant antibodies. Such methods use robots to pick and grid bacteria containing antibody genes, and a filter-based ELISA to screen and identify clones that express antibody fragments. Because liquid handling is eliminated and the clones are arrayed from master stocks, the same antibodies can be spotted multiple times and screened against multiple antigens simultaneously. Antibody arrays are highly useful in the identification of differentially expressed proteins. (See de Wildt et al. (2000) Nat Biotechnol 18:989–94.)

Differential expression of tapasin-like protein as detected using any of the above assays is diagnostic of adenofibromatous hyperplasia of the prostate, transitional cell carcinoma of the bladder, and adenocarcinoma, squamous cell carcinoma, and endobronchial carcinoid tumors of the lung. Such assays can be used with prostate tissue to distinguish adenofibromatous hyperplasia from benign prostatic hypertrophy and prostate intraepithelial neoplasia and with lung tissue, to distinguish lung cancer from asthma, chronic obstructive pulmonary disease, pneumonitis, and emphysema.

Therapeutics

As described in THE INVENTION section, chemical and structural similarity, in particular the sequences and specific motifs that exist between regions of the tapasin-like protein (SEQ ID NO:2) and mouse tapasin (SEQ ID NO:15), and chicken tapasin (SEQ ID NO:16). In addition, differential expression was demonstrated in cancers of the prostate, bladder and lung using transcript images. Thus, tapasin-like protein clearly plays a role in human cancers including, but not limited to, adenofibromatous hyperplasia of the prostate, transitional cell carcinoma of the bladder, and adenocarcinoma, squamous cell carcinoma, and endobronchial carcinoid tumors of the lung.

In one embodiment, a cancer which has decreased expression of the protein may be treated by the delivery of the protein or a composition thereof. Such delivery may be effected by methods well known in the art and include delivery by an antibody specifically targeted to the cancer.

In a second embodiment, an agonist which stimulates the expression or activity of the protein may be administered to a subject to treat a cancer. In an additional embodiment, a vector expressing the cDNA which encodes TLP may be delivered into the cancer cells of a subject in need of such treatment.

In a third embodiment, a vector expressing the cDNA which encodes TLP may be delivered into the cancer cells of a subject in need of such treatment.

In a fourth embodiment, a cancer which has increased expression of the protein may be treated by the delivery of an antibody, inhibitor, or antagonist. Such delivery may be effected by methods well known in the art.

In a fifth embodiment, a vector expressing the complement of the cDNA which encodes TLP may be delivered into the cancer cells of a subject in need of such treatment.

Any of these compositions may be administered in combination with other therapeutic agents. Selection of the agents for use in combination therapy may be made by one of ordinary skill in the art according to conventional pharmaceutical principles. A combination of therapeutic agents may act synergistically to affect treatment of a particular cancer at a lower dosage of each agent alone.

Modification of Gene Expression Using Nucleic Acids

Gene expression may be modified by designing complementary or antisense molecules (DNA, RNA, or PNA) to the control, 5', 3', or other regulatory regions of the gene encoding TLP. Oligonucleotides designed to inhibit transcription initiation are preferred. Similarly, inhibition can be achieved using triple helix base-pairing which inhibits the binding of polymerases, transcription factors, or regulatory molecules (Gee et al. In: Huber and Carr (1994) *Molecular and Immunologic Approaches*, Futura Publishing, Mt. Kisco N.Y., pp. 163–177). A complementary molecule may also be designed to block translation by preventing binding between ribosomes and mRNA. In one alternative, a library or plurality of cDNAs may be screened to identify those which specifically bind a regulatory, non-translated sequence.

Ribozymes, enzymatic RNA molecules, may also be used to catalyze the specific cleavage of RNA. The mechanism of ribozyme action involves sequence-specific hybridization of the ribozyme molecule to complementary target RNA followed by endonucleolytic cleavage at sites such as GUA, GUU, and GUC. Once such sites are identified, an oligonucleotide with the same sequence may be evaluated for secondary structural features which would render the oligonucleotide inoperable. The suitability of candidate targets may also be evaluated by testing their hybridization with complementary oligonucleotides using ribonuclease protection assays.

Complementary nucleic acids and ribozymes of the invention may be prepared via recombinant expression, in vitro or in vivo, or using solid phase phosphoramidite chemical synthesis. In addition, RNA molecules may be modified to increase intracellular stability and half-life by addition of flanking sequences at the 5' and/or 3' ends of the molecule or by the use of phosphorothioate or 2'O-methyl rather than phosphodiesterase linkages within the backbone of the molecule. Modification is inherent in the production of PNAs and can be extended to other nucleic acid molecules. Either the inclusion of nontraditional bases such as inosine, queosine, and wybutosine, or the modification of adenine, cytidine, guanine, thymine, and uridine with acetyl-, methyl-, thio-groups renders the molecule less available to endogenous endonucleases.

Screening and Purification Assays

The cDNA encoding TLP may be used to screen a library or a plurality of molecules or compounds for specific binding affinity. The libraries may be aptamers, DNA molecules, RNA molecules, PNAs, peptides, proteins such as transcription factors, enhancers, or repressors, and other ligands which regulate the activity, replication, transcription, or translation of the endogenous gene. The assay involves combining a polynucleotide with a library or plurality of molecules or compounds under conditions allowing specific binding, and detecting specific binding to identify at least one molecule which specifically binds the single-stranded or double-stranded molecule.

In one embodiment, the cDNA of the invention may be incubated with a plurality of purified molecules or compounds and binding activity determined by methods well known in the art, e.g., a gel-retardation assay (U.S. Pat. No. 6,010,849) or a commercially available reticulocyte lysate transcriptional assay. In another embodiment, the cDNA may be incubated with nuclear extracts from biopsied and/or cultured cells and tissues. Specific binding between the cDNA and a molecule or compound in the nuclear extract is initially determined by gel shift assay and may be later confirmed by recovering and raising antibodies against that molecule or compound. When these antibodies are added into the assay, they cause a supershift in the gel-retardation assay.

In another embodiment, the cDNA may be used to purify a molecule or compound using affinity chromatography methods well known in the art. In one embodiment, the cDNA is chemically reacted with cyanogen bromide groups on a polymeric resin or gel. Then a sample is passed over and reacts with or binds to the cDNA. The molecule or compound which is bound to the cDNA may be released from the cDNA by increasing the salt concentration of the flow-through medium and collected.

In a further embodiment, the protein or a portion thereof may be used to purify a ligand from a sample. A method for using a protein or a portion thereof to purify a ligand would involve combining the protein or a portion thereof with a sample under conditions to allow specific binding, detecting specific binding between the protein and ligand, recovering the bound protein, and using a chaotropic agent to separate the protein from the purified ligand.

In a preferred embodiment, TLP may be used to screen a plurality of molecules or compounds in any of a variety of screening assays. The portion of the protein employed in such screening may be free in solution, affixed to an abiotic or biotic substrate (e.g. borne on a cell surface), or located intracellularly. For example, in one method, viable or fixed prokaryotic host cells that are stably transformed with recombinant nucleic acids that have expressed and positioned a peptide on their cell surface can be used in screening assays. The cells are screened against a plurality or libraries of ligands, and the specificity of binding or formation of complexes between the expressed protein and the ligand can be measured. Depending on the particular kind of molecules or compounds being screened, the assay may be used to identify DNA molecules, RNA molecules, peptide nucleic acids, peptides, proteins, mimetics, agonists, antagonists, antibodies, immunoglobulins, inhibitors, and drugs or any other ligand, which specifically binds the protein.

In one aspect, this invention comtemplates a method for high throughput screening using very small assay volumes and very small amounts of test compound as described in U.S. Pat. No. 5,876,946, incorporated herein by reference. This method is used to screen large numbers of molecules and compounds via specific binding. In another aspect, this invention also contemplates the use of competitive drug screening assays in which neutralizing antibodies capable of binding the protein specifically compete with a test compound capable of binding to the protein. Molecules or compounds identified by screening may be used in a model system to evaluate their toxicity, diagnostic, or therapeutic potential.

Pharmacology

Pharmaceutical compositions contain active ingredients in an effective amount to achieve a desired and intended purpose and a pharmaceutical carrier. The determination of an effective dose is well within the capability of those skilled in the art. For any compound, the therapeutically effective dose may be estimated initially either in cell culture assays or in animal models. The animal model is also used to achieve a desirable concentration range and route of administration. Such information may then be used to determine useful doses and routes for administration in humans.

A therapeutically effective dose refers to that amount of protein or inhibitor which ameliorates the symptoms or condition. Therapeutic efficacy and toxicity of such agents may be determined by standard pharmaceutical procedures in cell cultures or experimental animals, e.g., $ED_{50}$ (the dose therapeutically effective in 50% of the population) and $LD_{50}$ (the dose lethal to 50% of the population). The dose ratio between toxic and therapeutic effects is the therapeutic index, and it may be expressed as the ratio, $LD_{50}/ED_{50}$. Pharmaceutical compositions which exhibit large therapeutic indexes are preferred. The data obtained from cell culture assays and animal studies are used in formulating a range of dosage for human use.

Model Systems

Animal models may be used as bioassays where they exhibit a phenotypic response similar to that of humans and where exposure conditions are relevant to human exposures. Mammals are the most common models, and most infectious agent, cancer, drug, and toxicity studies are performed on rodents such as rats or mice because of low cost, availability, lifespan, reproductive potential, and abundant reference literature. Inbred and outbred rodent strains provide a convenient model for investigation of the physiological consequences of under- or over-expression of genes of interest and for the development of methods for diagnosis and treatment of diseases. A mammal inbred to over-express a particular gene (for example, secreted in milk) may also serve as a convenient source of the protein expressed by that gene.

Toxicology

Toxicology is the study of the effects of agents on living systems. The majority of toxicity studies are performed on rats or mice. Observation of qualitative and quantitative changes in physiology, behavior, homeostatic processes, and lethality in the rats or mice are used to generate a toxicity profile and to assess potential consequences on human health following exposure to the agent.

Genetic toxicology identifies and analyzes the effect of an agent on the rate of endogenous, spontaneous, and induced genetic mutations. Genotoxic agents usually have common chemical or physical properties that facilitate interaction with nucleic acids and are most harmful when chromosomal aberrations are transmitted to progeny. Toxicological studies may identify agents that increase the frequency of structural or functional abnormalities in the tissues of the progeny if administered to either parent before conception, to the mother during pregnancy, or to the developing organism. Mice and rats are most frequently used in these tests because their short reproductive cycle allows the production of the numbers of organisms needed to satisfy statistical requirements.

Acute toxicity tests are based on a single administration of an agent to the subject to determine the symptomology or lethality of the agent. Three experiments are conducted: 1) an initial dose-range-finding experiment, 2) an experiment to narrow the range of effective doses, and 3) a final experiment for establishing the dose-response curve.

Subchronic toxicity tests are based on the repeated administration of an agent. Rat and dog are commonly used in these studies to provide data from species in different families. With the exception of carcinogenesis, there is considerable evidence that daily administration of an agent at high-dose concentrations for periods of three to four months will reveal most forms of toxicity in adult animals.

Chronic toxicity tests, with a duration of a year or more, are used to demonstrate either the absence of toxicity or the carcinogenic potential of an agent. When studies are conducted on rats, a minimum of three test groups plus one control group are used, and animals are examined and monitored at the outset and at intervals throughout the experiment.

Transgenic Animal Models

Transgenic rodents that over-express or under-express a gene of interest may be inbred and used to model human diseases or to test therapeutic or toxic agents. (See, e.g., U.S. Pat. No. 5,175,383 and U.S. Pat. No. 5,767,337.) In some cases, the introduced gene may be activated at a specific time in a specific tissue type during fetal or postnatal development. Expression of the transgene is monitored by analysis of phenotype, of tissue-specific mRNA expression, or of serum and tissue protein levels in transgenic animals before, during, and after challenge with experimental drug therapies.

Embryonic Stem Cells

Embryonic (ES) stem cells isolated from rodent embryos retain the potential to form embryonic tissues. When ES cells are placed inside a carrier embryo, they resume normal development and contribute to tissues of the live-born animal. ES cells are the preferred cells used in the creation of experimental knockout and knockin rodent strains. Mouse ES cells, such as the mouse 129/SvJ cell line, are derived from the early mouse embryo and are grown under culture conditions well known in the art. Vectors used to produce a transgenic strain contain a disease gene candidate and a marker gen, the latter serves to identify the presence of the introduced disease gene. The vector is transformed into ES cells by methods well known in the art, and transformed ES cells are identified and microinjected into mouse cell blastocysts such as those from the C57BL/6 mouse strain. The blastocysts are surgically transferred to pseudopregnant dams, and the resulting chimeric progeny are genotyped and bred to produce heterozygous or homozygous strains.

ES cells derived from human blastocysts may be manipulated in vitro to differentiate into at least eight separate cell lineages. These lineages are used to study the differentiation of various cell types and tissues in vitro, and they include endoderm, mesoderm, and ectodermal cell types which differentiate into, for example, neural cells, hematopoietic lineages, and cardiomyocytes.

Knockout Analysis

In gene knockout analysis, a region of a gene is enzymatically modified to include a non-mammalian gene such as the neomycin phosphotransferase gene (neo; Capecchi (1989) Science 244:1288–1292). The modified gene is transformed into cultured ES cells and integrates into the endogenous genome by homologous recombination. The inserted sequence disrupts transcription and translation of the endogenous gene. Transformed cells are injected into rodent blastulae, and the blastulae are implanted into pseudopregnant dams. Transgenic progeny are crossbred to obtain homozygous inbred lines which lack a functional copy of the mammalian gene. In one example, the mammalian gene is a human gene.

Knockin Analysis

ES cells can be used to create knockin humanized animals (pigs) or transgenic animal models (mice or rats) of human diseases. With knockin technology, a region of a human gene is injected into animal ES cells, and the human sequence integrates into the animal cell genome. Transformed cells are injected into blastulae and the blastulae are implanted as described above. Transgenic progeny or inbred lines are studied and treated with potential pharmaceutical agents to obtain information on treatment of the analogous human condition. These methods have been used to model several human diseases.

Non-Human Primate Model

The field of animal testing deals with data and methodology from basic sciences such as physiology, genetics, chemistry, pharmacology and statistics. These data are paramount in evaluating the effects of therapeutic agents on non-human primates as they can be related to human health. Monkeys are used as human surrogates in vaccine and drug evaluations, and their responses are relevant to human exposures under similar conditions. Cynomolgus and Rhesus monkeys (*Macaca fascicularis* and *Macaca mulatta*, respectively) and Common Marmosets (*Callithrix jacchus*) are the most common non-human primates (NHPs) used in these investigations. Since great cost is associated with developing and maintaining a colony of NHPs, early research and toxicological studies are usually carried out in rodent models. In studies using behavioral measures such as drug addiction, NHPs are the first choice test animal. In addition, NHPs and individual humans exhibit differential sensitivities to many drugs and toxins and can be classified as a range of phenotypes from "extensive metabolizers" to "poor metabolizers" of these agents.

In additional embodiments, the cDNAs which encode the protein may be used in any molecular biology techniques that have yet to be developed, provided the new techniques rely on properties of cDNAs that are currently known, including, but not limited to, such properties as the triplet genetic code and specific base pair interactions.

EXAMPLES

I cDNA Library and Sequence Preparation

A pooled sample of bone marrow from the breast bones of 24 males and females of Caucasian heritage whose ages ranged from 16 to 70 years was used to obtain poly A+RNA (Clontech Laboratories, Palo Alto Calif.). The poly A+RNA was used to construct the cDNA library, BMARNOT02 (Stratagene). cDNA synthesis was primed using both oligo d(T) and random hexamers, and the two cDNA preparations were processed separately. Synthetic adapter oligonucleotides were ligated onto the cDNAs enabling their insertion into the UNI-ZAP vector system (Stratagene). Blue/white color selection enabled the detection of clones with cDNA inserts.

The phagemid forms of individual cDNA clones were obtained by the in vivo excision process, in which the host bacterial strain was co-infected with both the library phage and an f1 helper phage. Enzymes derived from the library-containing phage and the helper phage nicked the DNA, initiated new DNA synthesis from defined sequences on the target DNA, and created a smaller, single stranded circular phagemid DNA molecule that included all DNA sequences of the PBLUESCRIPT phagemid and the cDNA insert. The phagemid DNA was released from the cells, purified, and used to reinfect fresh SOLR host cells (Stratagene). Because the phagemid carried the gene for β-lactamase, newly transformed bacteria were selected on medium containing ampicillin. Then, the two cDNA preparations were combined into a single library by mixing equal numbers of bacteriophage.

The quality of the cDNA library was assessed using DNA probes, and the PBLUESCRIPT phagemid (Stratagene) was excised and infected into *E. coli* host strain XL1-BLUE (Stratagene) where double-stranded phagemid DNA was produced. cDNAs were obtained using either the QIAWELL-8 plasmid or QIAGEN DNA purification system (QIAGEN, Chatsworth Calif.). The DNA was eluted from the purification resin and prepared for DNA sequencing and other analytical manipulations.

II Identification, Extension, Assembly, and Analyses of the Sequences

Incyte clone 700124888 (SEQ ID NO:14) from ZOOSEQ database (Incyte Genomics) of rat cDNA sequences was used to identify sequences in the LIFESEQ databases (Incyte Genomics) related to rat vesicle associated membrane protein (VAMP-1; g207628). The first pass extended cDNAs, and shotgun sequences, SEQ ID Nos:3–9 were assembled using Phrap. The assembled sequence, SEQ ID NO:1 was translated MACDNASIS PRO software (Hitachi Software Engineering) to elucidate the coding region, SEQ ID NO:2. The nucleotide and amino acid sequences were queried against databases such as the GenBank databases, SwissProt, BLOCKS, PRINTS, Prosite, and PFAM using BLAST. Motifs (source) and HMM algorithms were used to perform functional analyses, and the antigenic index (Jameson-Wolf analysis) was determined using LASER-GENE software (DNASTAR). Then, the clones and assembled sequence were compared using BLAST across all libraries to identify homologous sequences, SEQ ID NOs:10–13.

III Sequencing

The cDNAs were prepared for sequencing using the MICROLAB 2200 system (Hamilton) in combination with the DNA ENGINE thermal cyclers (MJ Research). The cDNAs were sequenced by the method of Sanger and Coulson (1975; J Mol Biol 94:441–448) using an ABI PRISM 373 or 377 sequencing system (ABI). Most of the isolates were sequenced according to standard ABI protocols and kits with solution volumes of 0.25x–1.0x concentrations or using solutions and dyes from APB.

IV Extension of cDNA Sequences

The cDNA sequence is extended to full length using the nucleotide sequence available in SEQ ID NO:3. Sequencing reactions were performed with the ABI PRISM Dye Terminator cycle sequencing kit with AMPLITAQ FS DNA polymerase (ABI). PCR is performed on a DNA ENGINE thermal cycler (MJ Research). Reactions were analyzed on an ABI PRISM 310 genetic analyzer (ABI). Individual sequences were assembled and edited using ABI AutoAssembler software (ABI).

In the alternative, extension is accomplished using oligonucleotide primers synthesized to initiate 5' and 3' extension of the known fragment. These primers are designed using commercially available primer analysis software to be about 22 to 30 nucleotides in length, to have a GC content of about 50% or more, and to anneal to the target sequence at temperatures of about 68 C to about 72 C. Any stretch of nucleotides that would result in hairpin structures and primer—primer dimerizations is avoided.

Selected cDNA libraries are used as templates to extend the sequence. If more than one extension is necessary, additional or nested sets of primers are designed. Preferred libraries have been size-selected to include larger cDNAs and random primed to contain more sequences with 5' or upstream regions of genes. Genomic libraries are used to obtain regulatory elements, especially extension into the 5' promoter binding region.

High fidelity amplification is obtained by PCR using methods such as that taught in U.S. Pat. No. 5,932,451. PCR is performed in 96-well plates using the DNA ENGINE thermal cycler (MJ Research). The reaction mix contains DNA template, 200 nmol of each primer, reaction buffer containing $Mg^{2+}$, $(NH_4)_2SO_4$, and β-mercaptoethanol, Taq DNA polymerase (APB), ELONGASE enzyme (Life Technologies), and Pfu DNA polymerase (Stratagene), with the following parameters for primer pair PCI A and PCI B (Incyte Genomics): Step 1: 94 C, three min; Step 2: 94 C, 15 sec; Step 3: 60 C, one min; Step 4: 68 C, two min; Step 5: Steps 2, 3, and 4 repeated 20 times; Step 6: 68 C, five min; Step 7: storage at 4 C. In the alternative, the parameters for primer pair T7 and SK+(Stratagene) are as follows: Step 1: 94 C, three min; Step 2: 94 C, 15 sec; Step 3: 57 C, one min; Step 4: 68 C, two min; Step 5: Steps 2, 3, and 4 repeated 20 times; Step 6: 68 C, five min; Step 7: storage at 4 C.

The concentration of DNA in each well is determined by dispensing 100 μl PICOGREEN quantitation reagent (0.25% reagent in 1x TE, v/v; Molecular Probes) and 0.5 μl of undiluted PCR product into each well of an opaque fluorimeter plate (Corning, Acton Mass.) and allowing the DNA to bind to the reagent. The plate is scanned in a Fluoroskan II (Labsystems Oy, Finland) to measure the fluorescence of the sample and to quantify the concentration of DNA. A 5 μl to 10 μl aliquot of the reaction mixture is analyzed by electrophoresis on a 1% agarose minigel to determine which reactions are successful in extending the sequence.

The extended clones are desalted, concentrated, transferred to 384-well plates, digested with CviJI cholera virus endonuclease (Molecular Biology Research, Madison Wis.), and sonicated or sheared prior to religation into pUC18 vector (APB). For shotgun sequences, the digested nucleotide sequences are separated on low concentration (0.6 to 0.8%) agarose gels, fragments are excised, and the agar is digested with AGARACE enzyme (Promega). Extended clones are religated using T4 DNA ligase (New England Biolabs) into pUC18 vector (APB), treated with Pfu DNA polymerase (Stratagene) to fill-in restriction site overhangs, and transfected into E. coli competent cells. Transformed cells are selected on antibiotic-containing media, and individual colonies are picked and cultured overnight at 37 C in 384-well plates in LB/2x carbenicillin liquid media.

The cells are lysed, and DNA is amplified using primers, Taq DNA polymerase (APB) and Pfu DNA polymerase (Stratagene) with the following parameters: Step 1: 94 C, three min; Step 2: 94 C, 15 sec; Step 3: 60 C, one min; Step 4: 72 C, two min; Step 5: steps 2, 3, and 4 repeated 29 times; Step 6: 72 C, five min; Step 7: storage at 4 C. DNA is quantified using PICOGREEN quantitation reagent (Molecular Probes) as described above. Samples with low DNA recoveries are reamplified using the conditions described above. Samples are diluted with 20% dimethylsulfoxide (DMSO; 1:2, v/v), and sequenced using DYENAMIC energy transfer sequencing primers and the DYENAMIC DIRECT cycle sequencing kit (APB) or the PRISM BIGDYE terminator cycle sequencing kit (ABI).

V Chromosome Mapping

Radiation hybrid and genetic mapping data available from public resources such as the Stanford Human Genome Center (SHGC), Whitehead Institute for Genome Research (WIGR), and Genethon are used to determine if any of the cDNAs presented in the Sequence Listing have been mapped. Any of the fragments of the cDNA encoding TLP that have been mapped result in the assignment of all related regulatory and coding sequences to the same location. The genetic map locations are described as ranges, or intervals, of human chromosomes. The map position of an interval, in cM (which is roughly equivalent to 1 megabase of human DNA), is measured relative to the terminus of the chromosomal p-arm.

VI Hybridization Technologies and Analyses ps Immobilization of cDNAs on a Substrate The cDNAs are applied to a substrate by one of the following methods. A mixture of cDNAs is fractionated by gel electrophoresis and transferred to a nylon membrane by capillary transfer. Alternatively, the cDNAs are individually ligated to a vector and inserted into bacterial host cells to form a library. The cDNAs are then arranged on a substrate by one of the following methods. In the first method, bacterial cells containing individual clones are robotically picked and arranged on a nylon membrane. The membrane is placed on LB agar containing selective agent (carbenicillin, kanamycin, ampicillin, or chloramphenicol depending on the vector used) and incubated at 37 C for 16 hr. The membrane is removed from the agar and consecutively placed colony side up in 10% SDS, denaturing solution (1.5 M NaCl, 0.5 M NaOH), neutralizing solution (1.5 M NaCl, 1 M Tris, pH 8.0), and twice in 2xSSC for 10 min each. The membrane is then UV irradiated in a STRATALINKER UV-crosslinker (Stratagene).

In the second method, cDNAs are amplified from bacterial vectors by thirty cycles of PCR using primers complementary to vector sequences flanking the insert. PCR amplification increases a starting concentration of 1–2 ng nucleic acid to a final quantity greater than 5 μg. Amplified nucleic acids from about 400 bp to about 5000 bp in length are purified using SEPHACRYL-400 beads (APB). Purified nucleic acids are arranged on a nylon membrane manually or using a dot/slot blotting manifold and suction device and are immobilized by denaturation, neutralization, and UV irradiation as described above. Purified nucleic acids are robotically arranged and immobilized on polymer-coated glass slides using the procedure described in U.S. Pat. No. 5,807, 522. Polymer-coated slides are prepared by cleaning glass microscope slides (Corning, Acton Mass.) by ultrasound in 0.1% SDS and acetone, etching in 4% hydrofluoric acid (VWR Scientific Products, West Chester Pa.), coating with 0.05% aminopropyl silane (Sigma Aldrich) in 95% ethanol, and curing in a 110 C oven. The slides are washed extensively with distilled water between and after treatments. The nucleic acids are arranged on the slide and then immobilized by exposing the array to UV irradiation using a STRATALINKER UV-crosslinker (Stratagene). Arrays are then washed at room temperature in 0.2% SDS and rinsed three times in distilled water. Non-specific binding sites are blocked by incubation of arrays in 0.2% casein in phosphate buffered saline (PBS; Tropix, Bedford Mass.) for 30 min at 60 C; then the arrays are washed in 0.2% SDS and rinsed in distilled water as before.

Probe Preparation for Membrane Hybridization

Hybridization probes derived from the cDNAs of the Sequence Listing are employed for screening cDNAs, mRNAs, or genomic DNA in membrane-based hybridizations. Probes are prepared by diluting the cDNAs to a concentration of 40–50 ng in 45 µl TE buffer, denaturing by heating to 100 C for five min, and briefly centrifuging. The denatured cDNA is then added to a REDIPRIME tube (APB), gently mixed until blue color is evenly distributed, and briefly centrifuged. Five µl of [$^{32}$P]dCTP is added to the tube, and the contents are incubated at 37 C for 10 min. The labeling reaction is stopped by adding 5 µl of 0.2M EDTA, and probe is purified from unincorporated nucleotides using a PROBEQUANT G-50 microcolumn (APB). The purified probe is heated to 100 C for five min, snap cooled for two min on ice, and used in membrane-based hybridizations as described below.

Probe Preparation for Polymer Coated Slide Hybridization

Hybridization probes derived from mRNA isolated from samples are employed for screening cDNAs of the Sequence Listing in array-based hybridizations. Probe is prepared using the GEMbright kit (Incyte Genomics) by diluting mRNA to a concentration of 200 ng in 9 µl TE buffer and adding 5 µl 5x buffer, 1 µl 0.1 M DTT, 3 µl Cy3 or Cy5 labeling mix, 1 µl RNase inhibitor, 1 µl reverse transcriptase, and 5 µl 1x yeast control mRNAs. Yeast control mRNAs are synthesized by in vitro transcription from non-coding yeast genomic DNA (W. Lei, unpublished). As quantitative controls, one set of control mRNAs at 0.002 ng, 0.02 ng, 0.2 ng, and 2 ng are diluted into reverse transcription reaction mixture at ratios of 1:100,000, 1:10,000, 1:1000, and 1:100 (w/w) to sample mRNA respectively. To examine mRNA differential expression patterns, a second set of control mRNAs are diluted into reverse transcription reaction mixture at ratios of 1:3, 3:1, 1:10, 10:1, 1:25, and 25:1 (w/w). The reaction mixture is mixed and incubated at 37 C for two hr. The reaction mixture is then incubated for 20 min at 85 C, and probes are purified using two successive CHROMA SPIN+TE 30 columns (Clontech). Purified probe is ethanol precipitated by diluting probe to 90 µl in DEPC-treated water, adding 2 µl 1 mg/ml glycogen, 60 µl 5 M sodium acetate, and 300 µl 100% ethanol. The probe is centrifuged for 20 min at 20,800xg, and the pellet is resuspended in 12 µl resuspension buffer, heated to 65 C for five min, and mixed thoroughly. The probe is heated and mixed as before and then stored on ice. Probe is used in high density array-based hybridizations as described below.

Membrane-Based Hybridization

Membranes are pre-hybridized in hybridization solution containing 1% Sarkosyl and 1x high phosphate buffer (0.5 M NaCi, 0.1 M Na$_2$HPO$_4$, 5 mM EDTA, pH 7) at 55 C for two hr. The probe, diluted in 15 ml fresh hybridization solution, is then added to the membrane. The membrane is hybridized with the probe at 55 C for 16 hr. Following hybridization, the membrane is washed for 15 min at 25 C in 1 mM Tris (pH 8.0), 1% Sarkosyl, and four times for 15 min each at 25 C in 1 mM Tris (pH 8.0). To detect hybridization complexes, XOMAT-AR film (Eastman Kodak, Rochester N.Y.) is exposed to the membrane overnight at −70 C, developed, and examined visually.

Polymer Coated Slide-Based Hybridization

Probe is heated to 65 C for five min, centrifuged five min at 9400 rpm in a 5415 C microcentrifuge (Eppendorf Scientific, Westbury N.Y.), and then 18 µl is aliquoted onto the array surface and covered with a coverslip. The arrays are transferred to a waterproof chamber having a cavity just slightly larger than a microscope slide. The chamber is kept at 100% humidity internally by the addition of 140 pl of 5×SSC in a corner of the chamber; The chamber containing the arrays is incubated for about 6.5 hr at 60 C. The arrays are washed for 10 min at 45 C in 1×SSC, 0.1% SDS, and three times for 10 min each at 45 C in 0.1×SSC, and dried.

Hybridization reactions are performed in absolute or differential hybridization formats. In the absolute hybridization format, probe from one sample is hybridized to array elements, and signals are detected after hybridization complexes form. Signal strength correlates with probe mRNA levels in the sample. In the differential hybridization format, differential expression of a set of genes in two biological samples is analyzed. Probes from the two samples are prepared and labeled with different labeling moieties. A mixture of the two labeled probes is hybridized to the array elements, and signals are examined under conditions in which the emissions from the two different labels are individually detectable. Elements on the array that are hybridized to equal numbers of probes derived from both biological samples give a distinct combined fluorescence (Shalon WO95/35505).

Hybridization complexes are detected with a microscope equipped with an Innova 70 mixed gas 10 W laser (Coherent, Santa Clara Calif.) capable of generating spectral lines at 488 nm for excitation of Cy3 and at 632 nm for excitation of Cy5. The excitation laser light is focused on the array using a 20X microscope objective (Nikon, Melville N.Y.). The slide containing the array is placed on a computer-controlled X-Y stage on the microscope and raster-scanned past the objective with a resolution of 20 micrometers. In the differential hybridization format, the two fluorophores are sequentially excited by the laser. Emitted light is split, based on wavelength, into two photomultiplier tube detectors (PMT R1477, Hamamatsu Photonics Systems, Bridgewater N.J.) corresponding to the two fluorophores. Filters positioned between the array and the photomultiplier tubes are used to separate the signals. The emission maxima of the fluorophores used are 565 nm for Cy3 and 650 nm for Cy5. The sensitivity of the scans is calibrated using the signal intensity generated by the yeast control mRNAs added to the probe mix. A specific location on the array contains a complementary DNA sequence, allowing the intensity of the signal at that location to be correlated with a weight ratio of hybridizing species of 1:100,000.

The output of the photomultiplier tube is digitized using a 12-bit RTI-835H analog-to-digital (A/D) conversion board (Analog Devices, Norwood Mass.) installed in an IBM-compatible PC computer. The digitized data are displayed as an image where the signal intensity is mapped using a linear 20-color transformation to a pseudocolor scale ranging from blue (low signal) to red (high signal). The data is also analyzed quantitatively. Where two different fluorophores are excited and measured simultaneously, the data are first corrected for optical crosstalk (due to overlapping emission spectra) between the fluorophores using the emission spectrum for each fluorophore. A grid is superimposed over the fluorescence signal image such that the signal from each spot is centered in each element of the grid. The fluorescence signal within each element is then integrated to obtain a numerical value corresponding to the average intensity of the signal. The software used for signal analysis is the GEMTOOLS program (Incyte Genomics).

VII Complementary Molecules

Molecules complementary to the cDNA, from about 5 (PNA) to about 5000 bp (complement of a cDNA insert), are used to detect or inhibit gene expression. Detection is described in Example VII. To inhibit transcription by preventing promoter binding, the complementary molecule is designed to bind to the most unique 5' sequence and includes nucleotides of the 5' UTR upstream of the initiation codon of the open reading frame. Complementary molecules include genomic sequences (such as enhancers or introns) and are used in "triple helix" base pairing to compromise the ability of the double helix to open sufficiently for the binding of polymerases, transcription factors, or regulatory molecules. To inhibit translation, a complementary molecule is designed to prevent ribosomal binding to the mRNA encoding the protein.

Complementary molecules are placed in expression vectors and used to transform a cell line to test efficacy; into an organ, tumor, synovial cavity, or the vascular system for transient or short term therapy; or into a stem cell, zygote, or other reproducing lineage for long term or stable gene therapy. Transient expression lasts for a month or more with a non-replicating vector and for three months or more if elements for inducing vector replication are used in the transformation/expression system.

Stable transformation of dividing cells with a vector encoding the complementary molecule produces a transgenic cell line, tissue, or organism (U.S. Pat. No. 4,736,866). Those cells that assimilate and replicate sufficient quantities of the vector to allow stable integration also produce enough complementary molecules to compromise or entirely eliminate activity of the cDNA encoding the protein.

VIII Expression of Tapasin-Like Protein

Expression and purification of the protein are achieved using either a mammalian or an insect cell expression system. The pUB6/V5-His vector system (Invitrogen, Carlsbad Calif.) is used to express tapasin-like protein in CHO cells. The vector contains the selectable bsd gene, multiple cloning sites, the promoter/enhancer sequence from the human ubiquitin C gene, a C-terminal V5 epitope for antibody detection with anti-V5 antibodies, and a C-terminal polyhistidine (6xHis) sequence for rapid purification on PROBOND resin (Invitrogen). Transformed cells are selected on media containing blasticidin.

*Spodoptera frugiperda* (Sf9) insect cells are infected with recombinant *Autographica californica* nuclear polyhedrosis virus (baculovirus). The polyhedrin gene is replaced with the cDNA by homologous recombination and the polyhedrin promoter drives cDNA transcription. The protein is synthesized as a fusion protein with 6xhis which enables purification as described above. Purified protein is used in the following activity and to make antibodies.

IX Production of Antibodies

Tapasin-like protein is purified using polyacrylamide gel electrophoresis and used to immunize mice or rabbits. Antibodies are produced using the protocols well known in the art and summarized below. Alternatively, the amino acid sequence of tapasin-like protein is analyzed using LASERGENE software (DNASTAR) to determine regions of high antigenicity. An antigenic epitope, usually found near the C-terminus or in a hydrophilic region is selected, synthesized, and used to raise antibodies. Typically, epitopes of about 15 residues in length are produced using an 431A peptide synthesizer (ABI) using Fmoc-chemistry and coupled to KLH (Sigma-Aldrich) by reaction with N-maleimidobenzoyl-N-hydroxysuccinimide ester to increase antigenicity.

Rabbits are immunized with the epitope-KLH complex in complete Freund's adjuvant. Immunizations are repeated at intervals thereafter in incomplete Freund's adjuvant. After a minimum of seven weeks for mouse or twelve weeks for rabbit, antisera are drawn and tested for antipeptide activity. Testing involves binding the peptide to plastic, blocking with 1% bovine serum albumin, reacting with rabbit antisera, washing, and reacting with radio-iodinated goat anti-rabbit IgG. Methods well known in the art are used to determine antibody titer and the amount of complex formation.

X Purification of Naturally Occurring Protein Using Specific Antibodies

Naturally occurring or recombinant protein is purified by immunoaffinity chromatography using antibodies which specifically bind the protein. An immunoaffinity column is constructed by covalently coupling the antibody to CNBr-activated SEPHAROSE resin (APB). Media containing the protein is passed over the immunoaffinity column, and the column is washed using high ionic strength buffers in the presence of detergent to allow preferential absorbance of the protein. After coupling, the protein is eluted from the column using a buffer of pH 2–3 or a high concentration of urea or thiocyanate ion to disrupt antibody/protein binding, and the protein is collected.

XI Screening Molecules for Specific Binding with the cDNA or Protein

The cDNA, or fragments thereof, or the protein, or portions thereof, are labeled with $^{32}$P-dCTP, Cy3-dCTP, or Cy5-dCTP (APB), or with BIODIPY or FITC (Molecular Probes, Eugene Oreg.), respectively. Libraries of candidate molecules or compounds previously arranged on a substrate are incubated in the presence of labeled cDNA or protein. After incubation under conditions for either a nucleic acid or amino acid sequence, the substrate is washed, and any position on the substrate retaining label, which indicates specific binding or complex formation, is assayed, and the ligand is identified. Data obtained using different concentrations of the nucleic acid or protein are used to calculate affinity between the labeled nucleic acid or protein and the bound molecule.

XII Two-Hybrid Screen

A yeast two-hybrid system, MATCHMAKER LexA Two-Hybrid system (Clontech Laboratories, Palo Alto Calif.), is used to screen for peptides that bind the protein of the invention. A cDNA encoding the protein is inserted into the multiple cloning site of a pLexA vector, ligated, and transformed into *E. coli*. cDNA, prepared from mRNA, is inserted into the multiple cloning site of a pB42AD vector, ligated, and transformed into *E. coli* to construct a cDNA library. The pLexA plasmid and pB42AD-cDNA library constructs are isolated from *E. coli* and used in a 2:1 ratio to co-transform competent yeast EGY48[p8op-lacZ] cells using a polyethylene glycol/lithium acetate protocol. Transformed yeast cells are plated on synthetic dropout (SD) media lacking histidine (-His), tryptophan (-Trp), and uracil (-Ura), and incubated at 30 C until the colonies have grown up and are counted. The colonies are pooled in a minimal volume of 1x TE (pH 7.5), replated on SD/-His/-Leu/-Trp/-Ura media supplemented with 2% galactose (Gal), 1% raffinose (Raf), and 80 mg/ml 5-bromo-4-chloro-3-indolyl β-d-galactopyranoside (X-Gal), and subsequently examined for growth of blue colonies. Interaction between expressed protein and cDNA fusion proteins activates expression of a LEU2 reporter gene in EGY48 and produces colony growth on media lacking leucine (-Leu). Interaction also activates expression of β-galactosidase from the p8op-lacZ porter construct that produces blue color in colonies grown on X-Gal.

Positive interactions between expressed protein and cDNA fusion proteins are verified by isolating individual positive colonies and growing them in SD/-Trp/-Ura liquid medium for 1 to 2 days at 30 C. A sample of the culture is plated on SD/-Trp/-Ura media and incubated at 30 C until colonies appear. The sample is replica-plated on SD/-Trp/-Ura and SD/-His/-Trp/-Ura plates. Colonies that grow on SD containing histidine but not on media lacking histidine have lost the pLexA plasmid. Histidine-requiring colonies are grown on SD/Gal/Raf/X-Gal/-Trp/-Ura, and white colonies are isolated and propagated. The pB42AD-cDNA plasmid, which contains a cDNA encoding a protein that physically interacts with the protein, is isolated from the yeast cells and characterized.

XIII Transcript Imaging

A transcript image was performed using the LIFESEQ GOLD database (Jun01release, Incyte Genomics). This process allowed assessment of the relative abundance of the expressed polynucleotides in more than 1400 cDNA libraries. Criteria for transcript imaging can be selected from category, number of cDNAs per library, library description, disease indication, clinical relevance of sample, and the like.

All sequences and cDNA libraries in the LIFESEQ database have been categorized by system, organ/tissue and cell type. For each category, the number of libraries in which the sequence was expressed were counted and shown over the total number of libraries in that category. In some transcript images, all normalized or subtracted libraries, which have high copy number sequences removed prior to processing, and all mixed or pooled tissues, which are considered non-specific in that they contain more than one tissue type or more than one subject's tissue, can be excluded from the analysis. Treated and untreated cell lines and/or fetal tissue data can also be disregarded or removed where clinical relevance is emphasized. Conversely, fetal tissue may be emphasized wherever elucidation of inherited disorders or differentiation of particular cells or organs from stem cells (such as nerves, heart or kidney) would be furthered by removing clinical samples from the analysis.

The transcript images for prostate, bladder, and lung are shown below. The first column shows library name; the second column, the number of cDNAs sequenced in that library; the third column, the description of the library; the fourth column, absolute abundance of the transcript in the library; and the fifth column, percentage abundance of the transcript in the library.

| | | Category: Male Reproductive (Prostate) | | |
|---|---|---|---|---|
| Library** | cDNAs | Description of Prostate Tissue | Abundance | % Abundance |
| PROSNOT07 | 3046 | AH*, mw/adenoCA PROSTUT05, 69M | 1 | 0.0328 |
| PROSTMT07 | 3104 | AH, mw/adenoCA, 73M | 1 | 0.0322 |
| PROSNOT26 | 3694 | prostate, mw/adenoCA, 65M | 1 | 0.0271 |
| PROSNOT18 | 3915 | AH, aw/bladder TC CA, 58M | 1 | 0.0255 |
| PROSTUT05 | 6818 | prostate tumor, adenoCA, 69M | 1 | 0.0147 |
| PROSNOT14 | 7656 | AH, mw/adenoCA PROSTUT08, 60M | 1 | 0.0131 |

*adenofibromatous hyperplasia
**Cell line, pooled, subtracted and normalized libraries were not used in this analysis.

SEQ ID NO:1 was not expressed in libraries made from prostate diagnosed with benign prostatic hypertrophy (PROSDIP01, PROSBPS05, PROSBPT03, PROSDIP02, and PROSDIP03), prostate intraepithelial neoplasia (PROETMP01, PROETMP02, PROETMP03, PROETMP04, PROETMP06 and PROETMP07) or characterized as cytologically normal (PROSNOP01, PROSNOP03, PROSNOT01, PROSNOT07, PROSNOT11, and PROSTMT03). In biopsied prostate tissue, SEQ ID NO:1 is diagnostic for adenofibromatous hyperplasia and the early stages of prostate cancer.

| | | Category: Urinary Tract (Bladder) | | |
|---|---|---|---|---|
| Library | cDNAs | Description of Bladder Tissue | Abundance | % Abundance |
| BLADTUE01 | 1131 | transitional cell CA, 67M, 5RP | 1 | 0.0884 |
| BLADTUT04 | 7872 | transitional cell CA, 60M | 3 | 0.0381 |

SEQ ID NO:1 was not expressed in libraries made from cytologically normal bladder tissue (BLADNOR01, BLADNOT01, BLADNOT03, BLADNOT04, BLADNOT05 (which is matched with BLADTUT04), BLADNOT06, BLADNOT08 and BLADNOT09). In biopsied bladder, SEQ ID NO:1 is diagnostic for transitional cell carcinoma of the bladder.

| Category: Respiratory System (Lung) | | | | |
|---|---|---|---|---|
| Library* | cDNAs | Description of Lung Tissue | Abundance | % Abundance |
| LUNGTMT03 | 1949 | lung, mw/adenoCA, 43M | 2 | 0.1026 |
| LUNPTUT02 | 3641 | lung tumor, pleura, 55F | 2 | 0.0549 |
| LUNGTUT03 | 5260 | lung tumor, squamous cell CA, 69M | 3 | 0.0479 |
| LUNLTUT04 | 2809 | lung tumor, squamous cell CA, 65F | 1 | 0.0356 |
| LUNGNOE02 | 3451 | lung, 35F, 5RP (no cytology) | 1 | 0.0290 |
| LUNGNOT25 | 3888 | lung, mw/endobronchial carcinoid, 33M | 1 | 0.0257 |
| LUNGTUT17 | 3950 | lung tumor, adenoCA, 53M | 1 | 0.0253 |
| LUNGTUT02 | 5226 | lung tumor, mets thyroid CA, 79M, | 1 | 0.0191 |
| LUNLTMT01 | 6670 | lung, mw/adenoCA, 63F | 1 | 0.0150 |

*Cell line, fetal, pooled, subtracted, and normalized libraries were not used in this analysis.

SEQ ID NO:1 was not expressed in libraries made from tissues designated cytologically normal (LUNGNOM01, LUNGNON03, LUNGNOP01, LUNGNOT01, LUNGNOT02, LUNGNOT03, LUNGNOT04, LUNGNOT18, LUNGNOT22, LUNGNOT23, LUNGNOT27, LUNGNOT28, LUNGNOT31, LUNGNOT34, LUNGNOT35, LUNGNOT37, LUNGNOT40 and LUNGTMT04), or from patients diagnosed with asthma (LUNGAST01, LUNGNOT33, LUNGNOT38, and LUNGNOT39), chronic obstructive pulmonary disease (LUNGNOT12 and LUNGNOT14), pneumonitis (LUNGNOT15) or emphysema (LUNGNOT20). In biopsied lung tissue, SEQ ID NO:1 is diagnostic for cancers of the lung including adenocarcinoma, squamous cell carcinoma, and endobronchial carcinoid tumors.

In assays using normal and cancerous standards and patient samples, the cDNA, an mRNA, tapasin-like protein or an antibody specifically binding the protein serves a clinically relevant diagnostic marker for cancers of the prostate, bladder, and lung.

XIV Demonstration of Protein Activity

TLP activity may be demonstrated by the binding of TLP to TAP using an in vitro assay (Ravichandran (1996) J Biol Chem 271:13300–03). TLP is radiolabeled with $^{35}$S, and a TAP binding substrate is prepared in the form of a glutathione S-transferase (GST)-TAP fusion protein. For each assay, approximately 2 mg of GST-TAP fusion protein absorbed to glutathione-agarose beads is incubated with varying amounts of $^{35}$S-labeled TLP in buffer for 3 hours at 4° C. The agarose beads are separated from the incubation by sedimentation and washed several times to remove unbound protein. TLP and other bound proteins are solubilized from the agarose beads by boiling in wash buffer and separated by SDS-polyacrylamide gel electrophoresis. Bound TLP is visualized by autoradiography, and the amount of radioactivity is proportional to the binding of activity of TLP in the assay.

All patents and publications mentioned in the specification are incorporated by reference herein. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention that are obvious to those skilled in the field of molecular biology or related fields are intended to be within the scope of the following claims.

What is claimed is:

1. A purified protein comprising a polypeptide selected from:
   a) an amino acid sequence of SEQ ID NO:2.

2. A composition comprising the protein of claim 1 and a pharmaceutical carrier.

3. A method for using a protein to screen a plurality of molecules or compounds to identify at least one ligand, the method comprising:
   a) combining the protein of claim 1 with the molecules or compounds under conditions to allow specific binding, and
   b) detecting specific binding, thereby identifying a ligand which specifically binds the protein.

4. The method of claim 3 wherein the molecules or compounds are selected from DNA molecules, RNA molecules, peptide nucleic acids, peptides, proteins, mimetics, agonists, antagonists, antibodies, immunoglobulins, inhibitors, and drugs.

5. A method of using a protein to prepare and purify polyclonal antibodies comprising:
   a) immunizing an animal with the protein of claim 1 under conditions to elicit antibody response,
   b) isolating animal antibodies,
   c) attaching the protein to a substrate,
   d) contacting the substrate with isolated antibodies under conditions to allow specific binding to the protein.

6. A substrate upon which the protein of claim 1 is immobilized.

7. A method for using a protein to detect differential expression in a sample, the method comprising:
   a) performing an assay to quantify the amount of protein of claim 1 in a sample;
   b) comparing the amount of protein to standards, thereby detecting differential expression of the protein in the sample.

8. The method of claim 7 wherein the assay is selected from two-dimensional polyacrylamide gel electrophoresis, enzyme-linked immunosorbent assays, radioimmunoassays, and fluorescence activated cell sorting.

9. The method of claim 7 wherein the sample is from prostate, bladder or lung.

10. A method for using a protein to identify an antibody that specifically binds the protein comprising:
    a) contacting a plurality of antibodies with the protein of claim 1 under conditions to allow specific binding,
    b) detecting specific binding between an antibody and the protein, thereby identifying an antibody that specifically binds the protein.

11. The method of claim 10, wherein the plurality of antibodies are selected from a single chain antibody, a polyclonal antibody, a monoclonal antibody, a recombinant antibody, a Fab fragment, and an F(ab')$_2$ fragment.

12. A method of using a protein to prepare a monoclonal antibody comprising:
    a) immunizing a animal with a protein of claim 1 under conditions to elicit an antibody response;
    b) isolating antibody-producing cells from the animal;
    c) fusing the antibody-producing cells with immortalized cells in culture to form monoclonal antibody producing hybridoma cells;
    d) culturing the hybridoma cells; and
    e) isolating monoclonal antibodies from culture.

* * * * *